(12) United States Patent
Hagy et al.

(10) Patent No.: US 11,045,165 B2
(45) Date of Patent: Jun. 29, 2021

(54) PROBE AND SYSTEM FOR USE WITH AN ULTRASOUND DEVICE

(71) Applicant: Soma Research, LLC, Greenville, SC (US)

(72) Inventors: M. Dexter Hagy, Greenville, SC (US); Stephen F. Ridley, Columbia, SC (US)

(73) Assignee: Soma Research, LLC, Greenville, SC (US)

( * ) Notice: Subject to any disclaimer, the term of this patent is extended or adjusted under 35 U.S.C. 154(b) by 1238 days.

(21) Appl. No.: 15/372,812

(22) Filed: Dec. 8, 2016

(65) Prior Publication Data

US 2017/0086782 A1    Mar. 30, 2017

Related U.S. Application Data

(60) Continuation of application No. 13/649,710, filed on Oct. 11, 2012, now Pat. No. 10,610,195, which is a
(Continued)

(51) Int. Cl.
*A61B 8/08* (2006.01)
*A61B 17/34* (2006.01)
(Continued)

(52) U.S. Cl.
CPC .......... *A61B 8/0841* (2013.01); *A61B 5/062* (2013.01); *A61B 8/4411* (2013.01);
(Continued)

(58) Field of Classification Search
None
See application file for complete search history.

(56) References Cited

U.S. PATENT DOCUMENTS

| 4,054,881 A | 10/1977 | Raab |
| 4,407,294 A | 10/1983 | Vilkomerson |

(Continued)

FOREIGN PATENT DOCUMENTS

| JP | 63-122911 A | 5/1988 |
| JP | 2006-346477 | 12/2006 |

(Continued)

OTHER PUBLICATIONS

SONIXGPS Specifications Sheet: Precision Ultrasound Guidance for Biopsies and Line Placements.
(Continued)

*Primary Examiner* — Jonathan Cwern
(74) *Attorney, Agent, or Firm* — Dority & Manning, P.A.,

(57) ABSTRACT

Disclosed are ultrasound devices and methods for use in guiding a subdermal probe during a medical procedure. A device can be utilized to guide a probe through the probe guide to a subdermal site. In addition, a device can include a detector in communication with a processor. The detector can recognize the location of a target associated with the probe. The processor can utilize the data from the detector and create an image of a virtual probe that can accurately portray the location of the actual probe on a sonogram of a subdermal area. In addition, disclosed systems can include a set of correlation factors in the processor instructions. As such, the virtual probe image can be correlated with the location of the actual probe.

33 Claims, 14 Drawing Sheets

Related U.S. Application Data division of application No. 12/885,832, filed on Sep. 20, 2010, now Pat. No. 8,425,425.

(51) Int. Cl.
*A61B 8/00* (2006.01)
*A61B 5/06* (2006.01)
*A61B 34/20* (2016.01)
*A61B 90/00* (2016.01)

(52) U.S. Cl.
CPC .......... *A61B 8/4422* (2013.01); *A61B 8/4455* (2013.01); *A61B 8/4483* (2013.01); *A61B 8/461* (2013.01); *A61B 17/3403* (2013.01); A61B 2017/3407 (2013.01); A61B 2017/3413 (2013.01); A61B 2034/2051 (2016.02); A61B 2090/062 (2016.02); A61B 2090/0811 (2016.02); A61B 2090/378 (2016.02)

(56) References Cited

U.S. PATENT DOCUMENTS

| | | |
|---|---|---|
| 4,622,644 A | 11/1986 | Hansen |
| 5,078,144 A | 1/1992 | Sekino et al. |
| 5,285,154 A | 2/1994 | Burreson |
| 5,351,004 A | 9/1994 | Daniels et al. |
| 5,425,382 A | 6/1995 | Golden et al. |
| 5,437,276 A | 8/1995 | Takada |
| 5,622,170 A | 4/1997 | Schulz |
| 5,647,373 A | 7/1997 | Paltieli |
| 5,833,608 A | 11/1998 | Acker |
| 5,879,297 A | 3/1999 | Haynor et al. |
| 5,899,860 A | 5/1999 | Pfeiffer et al. |
| 5,944,023 A | 8/1999 | Johnson et al. |
| 5,971,949 A | 10/1999 | Levin et al. |
| 6,019,724 A | 2/2000 | Gronningsaeter et al. |
| 6,129,668 A | 10/2000 | Haynore et al. |
| 6,138,681 A | 10/2000 | Chen et al. |
| 6,144,300 A | 11/2000 | Dames |
| 6,197,001 B1 | 3/2001 | Wilson et al. |
| 6,216,029 B1 | 4/2001 | Paltieli |
| 6,263,230 B1 | 7/2001 | Haynor et al. |
| 6,323,770 B1 | 11/2001 | Dames |
| 6,329,916 B1 | 12/2001 | Dames |
| 6,332,089 B1 | 12/2001 | Acker et al. |
| 6,418,335 B2 | 7/2002 | Avrin et al. |
| 6,419,653 B2 | 7/2002 | Edwards et al. |
| 6,427,079 B1 | 7/2002 | Schneider et al. |
| 6,484,118 B1 | 11/2002 | Govari |
| 6,592,520 B1 | 7/2003 | Peszynski et al. |
| 6,626,832 B1 | 9/2003 | Paltieli et al. |
| 6,690,159 B2 | 2/2004 | Burreson et al. |
| 6,690,693 B1 | 2/2004 | Ben-Haim et al. |
| 6,724,191 B1 | 4/2004 | Larsen |
| 6,733,458 B1 | 5/2004 | Steins et al. |
| 6,764,449 B2 | 7/2004 | Lee |
| 6,785,571 B2 | 8/2004 | Glossop |
| 6,786,870 B2 | 9/2004 | Miyaki et al. |
| 6,977,504 B2 | 12/2005 | Wright et al. |
| 7,244,234 B2 | 7/2007 | Ridley et al. |
| 7,387,626 B2 | 6/2008 | Edwards et al. |
| 7,414,404 B2 | 8/2008 | Keene |
| 7,662,128 B2 | 2/2010 | Salcudean et al. |
| 7,668,583 B2 | 2/2010 | Fegert et al. |
| 7,729,742 B2 | 6/2010 | Govari |
| 7,785,330 B2 | 8/2010 | Sherman et al. |
| 7,835,785 B2 | 11/2010 | Scully et al. |
| 8,152,724 B2 | 4/2012 | Ridley et al. |
| 8,644,907 B2 | 2/2014 | Hartmann et al. |
| 8,934,961 B2 | 1/2015 | Lakin et al. |
| 2002/0077752 A1 | 6/2002 | Burreson et al. |
| 2003/0040671 A1 | 2/2003 | Somogyi et al. |
| 2003/0163142 A1 | 8/2003 | Paltieli et al. |
| 2004/0097803 A1 | 5/2004 | Panescu |
| 2004/0097805 A1 | 5/2004 | Verard et al. |
| 2004/0143252 A1 | 7/2004 | Hurst |
| 2004/0250819 A1 | 12/2004 | Blair et al. |
| 2005/0272974 A1 | 12/2005 | Iddan |
| 2006/0142656 A1 | 6/2006 | Malackowski et al. |
| 2007/0038113 A1 | 2/2007 | Oonuki et al. |
| 2007/0049822 A1 | 3/2007 | Bunce et al. |
| 2007/0208255 A1 | 9/2007 | Ridley et al. |
| 2008/0214925 A1 | 9/2008 | Wilson et al. |
| 2008/0255475 A1 | 10/2008 | Kondrosky et al. |
| 2008/0275465 A1 | 11/2008 | Paul et al. |
| 2009/0156926 A1 | 6/2009 | Messerly et al. |
| 2009/0234328 A1 | 9/2009 | Cox et al. |
| 2009/0275833 A1* | 11/2009 | Ikeda .................. A61B 8/0833 600/443 |
| 2010/0036227 A1 | 2/2010 | Cox et al. |
| 2010/0060472 A1 | 3/2010 | Kimura et al. |
| 2010/0191224 A1 | 7/2010 | Butcher |
| 2010/0204569 A1 | 8/2010 | Burnside et al. |
| 2010/0204614 A1 | 8/2010 | Lindquiest et al. |
| 2010/0228119 A1 | 9/2010 | Brennan et al. |
| 2010/0234724 A1 | 9/2010 | Jacobsen et al. |
| 2011/0015533 A1 | 1/2011 | Cox et al. |
| 2011/0087105 A1 | 4/2011 | Ridley et al. |
| 2011/0087106 A1 | 4/2011 | Ridley et al. |
| 2011/0196248 A1 | 8/2011 | Grunwald |
| 2011/0282188 A1 | 11/2011 | Burnside et al. |
| 2011/0295108 A1 | 12/2011 | Cox et al. |
| 2012/0059270 A1 | 3/2012 | Grunwald |
| 2012/0071759 A1 | 3/2012 | Hagy et al. |
| 2012/0095319 A1 | 4/2012 | Krondrosky et al. |
| 2012/0143029 A1 | 6/2012 | Silverstein et al. |
| 2012/0157849 A1 | 6/2012 | Ridley et al. |
| 2012/0157855 A1 | 6/2012 | Ridley et al. |
| 2012/0220854 A1 | 8/2012 | Messerly et al. |
| 2013/0296691 A1 | 11/2013 | Ashe |
| 2013/0303896 A1 | 11/2013 | Kalpin et al. |
| 2013/0317338 A1 | 11/2013 | Silverstein |
| 2014/0094768 A1 | 4/2014 | Stangenes et al. |
| 2015/0005621 A1 | 1/2015 | Liu |

FOREIGN PATENT DOCUMENTS

| | | |
|---|---|---|
| WO | WO 1999/027837 | 6/1999 |
| WO | WO 2000/027281 | 5/2000 |
| WO | WO 2001/039683 | 6/2001 |
| WO | WO 2007/002541 | 1/2007 |
| WO | WO 2007/027470 | 3/2007 |
| WO | WO 2011/150376 | 12/2011 |
| WO | WO 2012/088535 | 6/2012 |
| WO | WO 2013/006817 | 1/2013 |
| WO | WO 2013/034175 | 3/2013 |
| WO | WO 2014/052894 | 4/2014 |
| WO | WO 2014/062728 | 4/2014 |

OTHER PUBLICATIONS

Ascension Technology's miniaturized magnetic sensors enable improved procedures, 1-5, Nov. 29, 2009 Virtual Medical Worlds Monthly.
Hagy et al., U.S. Appl. No. 13/649,710, filed Oct. 11, 2012, Probe and System for Use with an Ultrasound Device.
Ridley et al., U.S. Appl. No. 13/660,560, filed Oct. 25, 2012, Ultrasound Guided Probe Device and Methods of Using Same.
Hagy et al., U.S. Appl. No. 13/835,034, filed Mar. 15, 2013, Ultrasound Guidance System Including Tagged Probe Assembly.

* cited by examiner

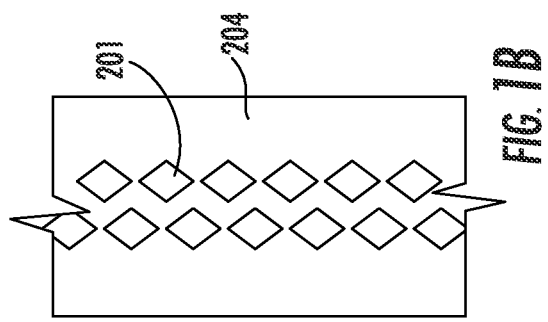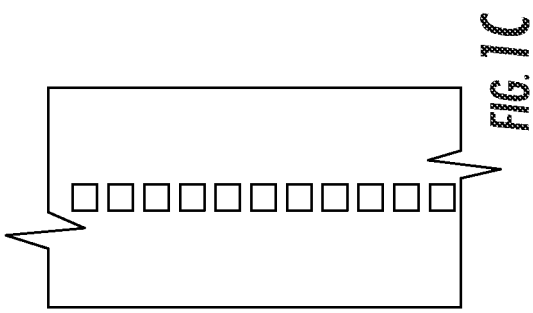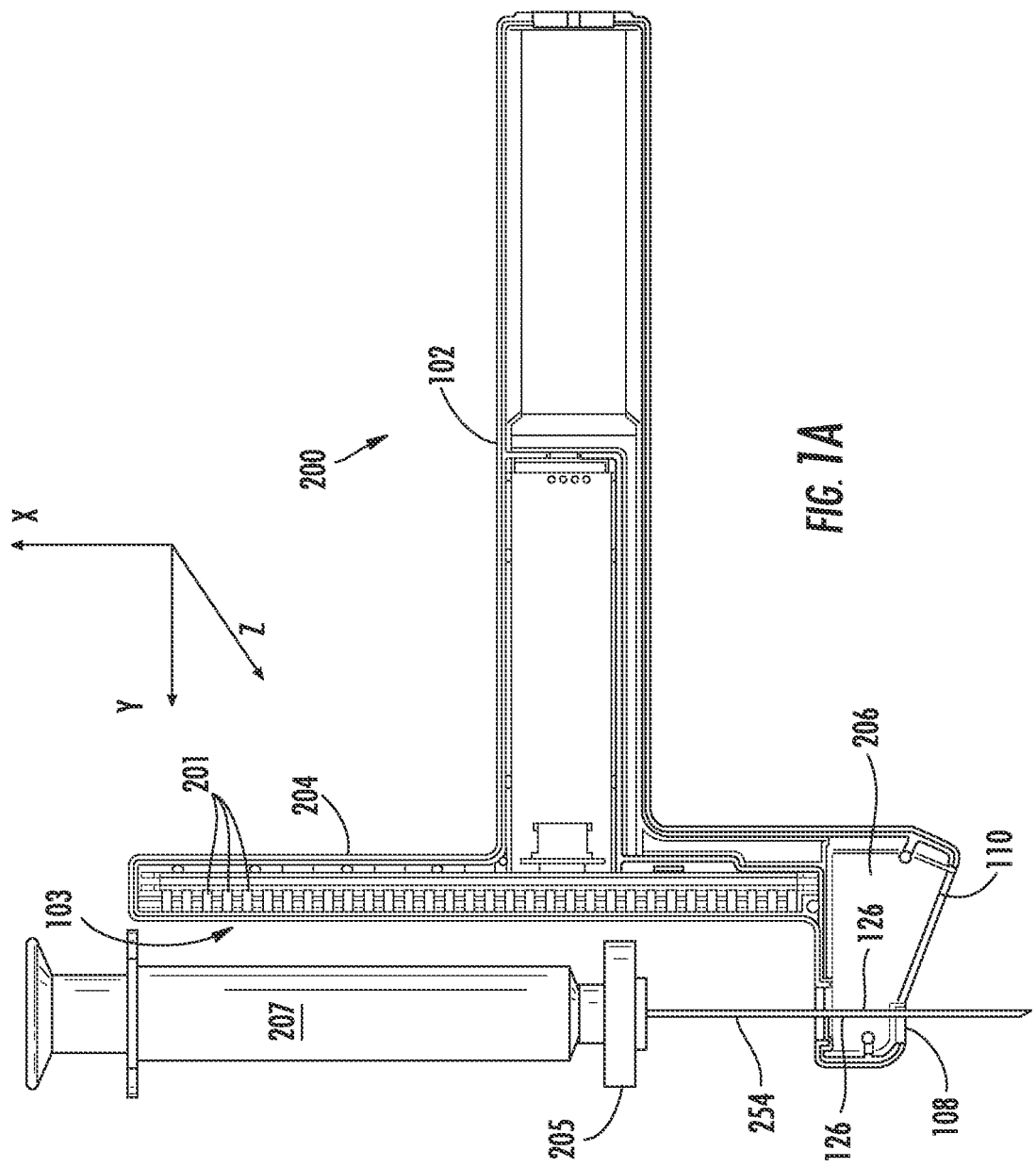

PROBE AND SYSTEM FOR USE WITH AN ULTRASOUND DEVICE

CROSS REFERENCE TO RELATED APPLICATION

The present application is continuation application of U.S. patent application Ser. No. 13/649,710, entitled "Probe and System for Use With an Ultrasound Device," having a filing date of Oct. 11, 2012, which is a divisional application of U.S. patent application Ser. No. 12/885,832, entitled "Virtual Image Formation Method for an Ultrasound Device," having a filing date of Sep. 20, 2010, all of which are hereby incorporated herein by reference in their entireties for all purposes. Any disclaimer that may have occurred during prosecution of the above-referenced application(s) is hereby expressly rescinded.

BACKGROUND OF THE INVENTION

Medical probe devices are utilized for many purposes, chief of which include catheterization, centesis, and biopsy procedures. Percutaneous placement of probes using these devices is often performed with techniques which rely on ascertaining the correct locations of palpable or visible structures. This is neither a simple nor a risk-free procedure. For instance, proper insertion and placement of a subdermal probe depends on correct localization of anatomical landmarks, proper positioning of the patient in relation to the care provider, and awareness of both the depth of the subdermal location and angle from the point of probe insertion. Risks of unsuccessful placement of a probe can range from minor complications, such as patient anxiety and discomfort due to repetition of the procedure following incorrect initial placement, to severe complications, such as pneumothorax, arterial or venous laceration, or delay of delivery of life-saving fluids or medications in an emergency situation.

Ultrasound guided techniques and devices have been developed to aid in correct placement of percutaneous probes. Ultrasound guided techniques often utilize two people, an ultrasound operator who locates the internal site and keeps an image of the site centrally located on a monitor, and a care provider who attempts to guide the probe to the site based upon the sonogram. Such techniques are very difficult perceptually. For instance, these techniques are complicated by the fact that the person guiding the probe to the internal site is not the same person as is operating the ultrasound. In addition, the generally thin, cylindrical probe is usually small and reflects very little of the ultrasound beam. Moreover, as the cylindrical probe and the ultrasound beam are not generally normal to one another, the small amount of ultrasonic energy that is reflected from the probe will reflect at an angle to the incident beam, resulting in little if any of the reflected energy being detected by the ultrasound transducer. As a result, the probe itself is difficult to visualize in the sonogram and the person placing the probe must attempt to guide the probe to the correct location using minimal visual feedback. For example, the only visual feedback available is often only subtle artifacts of the motion of the probe such as slight changes in the sonogram as the probe deflects and penetrates the surrounding tissue. The trained observer can pick up subtle ultrasonic shadow artifacts deep to the probe created when the probe blocks the transmission of the ultrasound beam to the tissue below, and such subtle artifacts can be used to help guide the probe to the desired subdermal location.

In an attempt to relieve the difficulties of ultrasound guided probe techniques, systems have been developed including a probe guide which can be attached to an ultrasound transducer housing. Problems still exist with such devices however. For instance, the probe is often inserted at angle that crosses the scanned plane displayed on the sonogram, restricting the intersection of the scanned plane and the point of the probe to a very small area in space. In addition, even if the probe passes for a length in line with the scanned plane, very little, if any, ultrasonic energy is reflected from the probe back to the transducer. In fact, due to the lack of reflection off of the probe, visual cues to the location of the probe tip may be even more difficult to discern on a sonogram when using these devices. In addition, in many of these devices, the probe passes through the ultrasound beam at a fixed depth range depending on the set angle of the probe guide, and this may not correspond to the depth of the desired subdermal site, in which case it may not be possible to show the juncture of the desired site and the probe tip on the sonogram at all.

What are needed in the art are improved ultrasound devices and methods for using such devices. For instance, what are needed in the art are ultrasound devices that can be utilized by a single operator to accurately visualize the delivery of a probe to a subdermal location.

SUMMARY OF THE INVENTION

According to one embodiment, disclosed is a method for guiding a probe tip to a subdermal site. For instance, a method can include guiding a probe through a probe guide of an ultrasound device. The ultrasound device can include an ultrasound transducer and a detector, both in communication with a processor. The detector can determine the location of a target that is associated with the probe.

A method can also include configuring the processor to determine the location of a virtual probe tip from the location of the target as determined by the detector and communicated to the processor. Specifically, the processor can execute instructions provided via software to determine the location of the virtual probe tip. The instructions can include a set of correlation factors that correlate the location of the virtual probe tip as determined by the processor with the subdermal location of the probe tip.

A method can also include forming a sonogram of the subdermal site on a monitor from information communicated to the processor from the ultrasound transducer, and forming an image on the sonogram of the location of the virtual probe tip as determined and correlated by the processor from information communicated to the processor from the detector.

A method can also include configuring the processor to determine when a probe has been flexed such that it is out of alignment with the probe guide. For instance, the processor software can determine an index level that can indicate movement of the target away from the detector. Moreover, the processor can trigger an alarm when the index level exceeds a predetermined value, indicating that the target associated with the probe has been moved too far from the detector.

Also disclosed herein is an ultrasound device that can include an ultrasound transducer, a detector, and a processor. For instance, the detector can include an array of sensors. In one preferred embodiment, the sensors can be Hall effect transducers and the target that is associated with the probe for use with the device can be a magnet.

An ultrasound device can include additional components as well. For example, a device can include an alarm that can be triggered when a probe is flexed out of alignment with the probe guide (e.g., the index level determined by the processor exceeds a predetermined value). An ultrasound device can also include features such as one or more of a sterilizable shield that encloses at least a portion of the ultrasound device, and a clamp for clamping a probe within the probe guide.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 1A illustrates an ultrasound device including a series of Hall effect sensors along a length of the ultrasound device.

FIGS. 1B and 1C illustrate two embodiments of arrays of Hall effect sensors as may be utilized in disclosed ultrasound devices.

Figure 2:
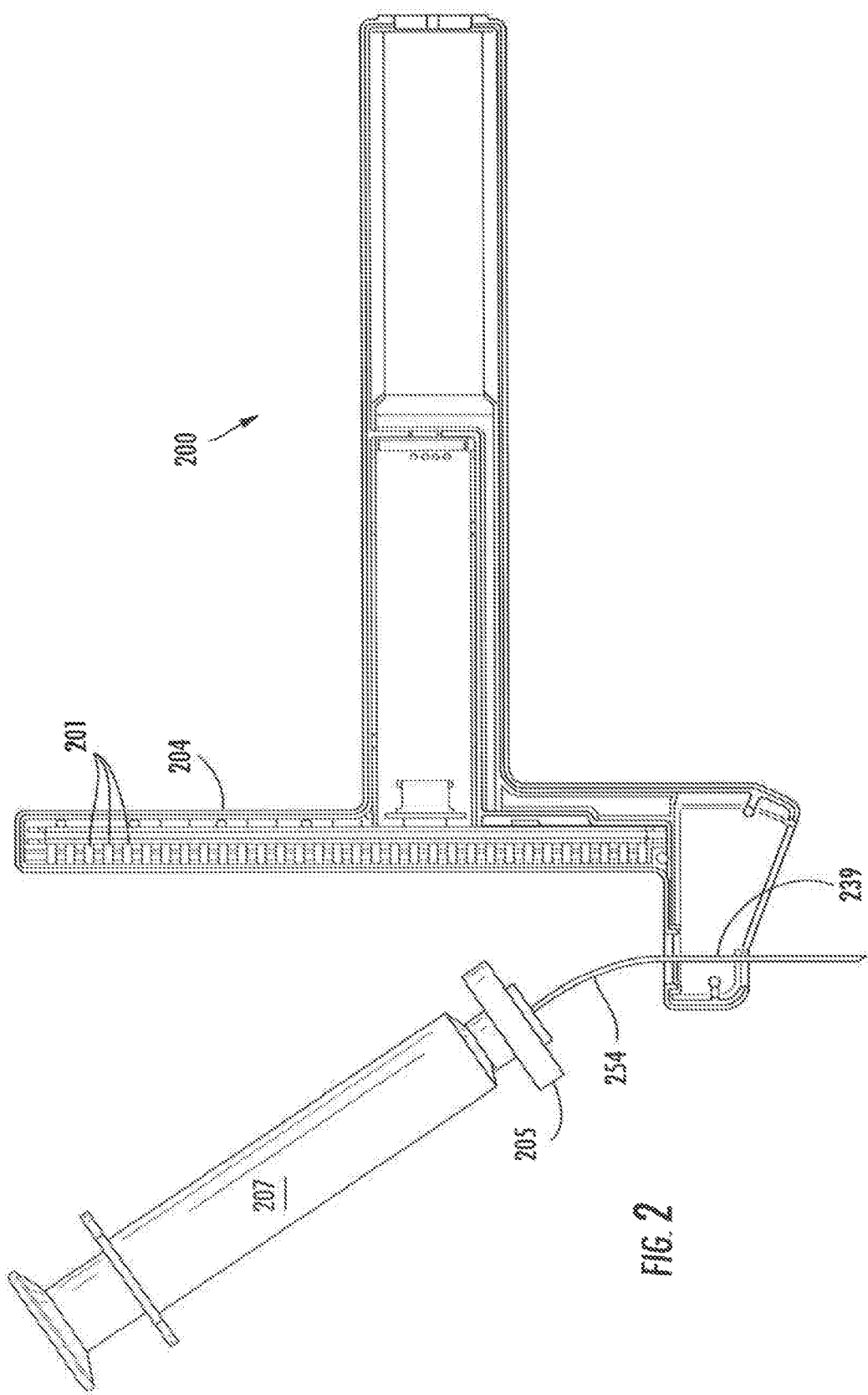
FIG. 2 illustrates the ultrasound device of FIG. 1A upon deformation of a probe during use.

Repeat use of reference characters in the present specification and drawings is intended to represent the same or analogous features of elements of the disclosed subject matter. Other objects, features and aspects of the subject matter are disclosed in or are obvious from the following detailed description.

DETAILED DESCRIPTION OF PREFERRED EMBODIMENTS

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

Definitions

As utilized herein, the term "probe" generally refers to an item that can be guided to a subdermal location, for instance for delivery of a therapeutic, e.g., a compound or a treatment, to the location; for removal of material from the location; and so forth. For example, the term "probe" can refer to a needle, a tube, a biopsy needle or blade, or any other item that can be guided to a subdermal location. In general, a probe can be guided by and used in conjunction with an ultrasound device as described herein. A probe can define a ratio of the length of the probe to the diameter (or a width) of the probe greater than about 10. Moreover, a probe can define any cross sectional shape, e.g., round, square, oblong, triangular, rectangular, etc.

As utilized herein, the term "ultrasound device" generally refers to a device that includes an ultrasound transducer therein and that can be utilized in conjunction with a probe, but does not necessarily include the probe itself. For instance, an ultrasound device can include a probe guide as an attachable or permanent component of the ultrasound device, and a probe can be utilized in conjunction with the ultrasound device to access a subdermal site by guiding the probe through the probe guide of the ultrasound device.

DETAILED DESCRIPTION

According to one embodiment, disclosed herein are ultrasound devices and methods for use in accurately forming a virtual image of a probe in conjunction with a sonogram during a medical procedure. More specifically, disclosed herein are ultrasound devices that can include a detector for detecting the location of a target associated with a probe while the probe is held or moved within a probe guide of the ultrasound device. A detector can be in communication with a processor that can utilize information received from the detector with regard to target location and accurately identify the location of the probe tip based upon the information. A processor can also be in communication with a monitor and can create an image of a virtual probe on the monitor, for instance in conjunction with a sonogram. Beneficially, disclosed ultrasound devices can accurately correlate the image of the virtual probe tip with the location of the actual subdermal probe tip.

Utilizing an ultrasound device incorporating a probe guide, a probe can be guided such that the probe tip approaches a subdermal site that can be visualized on the scanned plane of a sonogram. For instance, the probe tip can travel on a path that defines a known correlation with sound waves emitted by the ultrasound transducer, e.g., coincident in the scanned plane, parallel to the scanned plane, or intersecting the scanned plane at a point. When utilizing the ultrasound device, the path of the probe to the subdermal site can be known: the probe will advance toward the subdermal site on a straight line and at a predetermined angular relationship to the ultrasound housing base from the probe guide opening to the subdermal site that is imaged by the ultrasound. Thus, the path of the probe and the scanned plane of the sonogram image can both be defined by the orientation of the ultrasound transducer and can be coordinated on the subdermal site. In order to strike the site, the probe tip can be guided along this known path the desired distance. Beneficially, an ultrasound device can be formed so as to be conveniently utilized by a single operator who can insert a probe using a probe guidance system and also control the ultrasound transducer so as to see the sonogram and a virtual image of the probe overlaid on the sonogram in real time during the procedure.

An ultrasound device can incorporate a visualization system that can be used to create an image of a virtual probe that accurately correlates with the actual probe as it is being guided to a subdermal site and while it is being held at the site. Through utilization of a visualization system, the path of a probe and hence the location of the probe tip can be more clearly known in relation to subdermal site imaged by an ultrasound device.

In accord with the present disclosure, an ultrasound device can include a detector that can register the location of a target that is associated with the probe in the probe guide. This information can be electronically communicated to a processor and processed with input data (e.g., the length of the probe, etc.) and displayed as a real time image of a virtual probe in conjunction with a sonogram, i.e., the two images, the image developed from the data obtained by the detector, and the sonogram developed from the data obtained from the ultrasound transducer, can be displayed on the same monitor. Because the virtual probe location is correlated with the actual probe location, the location of the probe tip in relation to the subdermal site and the striking of the subdermal site by the probe tip can be seen in real time by an operator watching the virtual probe on the monitor during the procedure.

In general, any suitable detector can be utilized in disclosed devices for detecting the target that is associated with the probe. For instance, a detector can utilize infrared (IR), ultrasound, optical, laser, magnetic, or other detection mechanisms. In addition, the location of a detector is not critical to a device, save that it is capable of detecting the target that is associated with the probe. In addition, the target can be any suitable item. It can be all or a portion of the probe itself, or can be directly or indirectly attached to the probe.

FIG. 1A illustrates one embodiment of a magnetic based detection system as may be utilized. As can be seen, an ultrasound device 200 can include a handle 102, a post 204, and a base 206. The base 206 can define a probe guide 126 therethrough. An ultrasound transducer 110 that transmits and receives ultrasonic waves can be located in base 106. An ultrasound device 200 can include a series of sensors 201 that form a detector along a length of post 204. Sensors can be sensitive to the presence of a target 205 that can be attachable to a probe 254 which can be, for example, a needle. In the magnetic based detection system, sensors 201 can be Hall effect sensors that are sensitive to a magnetic field and target 205 can include one or more magnets. One exemplary embodiment of a magnetic based detection system as may be incorporated in disclosed devices is describe in U.S. Pat. No. 6,690,159 to Burreson, et al., which is incorporated herein by reference.

The sensors 201 can be arranged in one or more rows extending lengthwise along the post 204, which is the direction along which the probe will move during insertion, herein defined as the X direction, as shown in FIG. 1A. As is known, the presence of a magnetic field can induce a voltage in a Hall effect sensor that is proportional to the size of the magnetic field. The voltage of each sensor 201 can be electronically scanned and processed to determine the location of the target 205 relative to the sensing array (i.e., the detector). Processing can include grouping the sensors 201 and providing their outputs to a series of multiplexers which, in turn, are connected to a processor including software for analyzing the outputs and determining the location of the target 205 with regard to the entire sensor array. As the distance from the target 205 to the tip of the probe 254 is constant and known, the processor can likewise compute the location of the tip of probe 254.

The processing of the sensor outputs can include determining which sensor 201 has the highest (or lowest, depending upon the magnetic field orientation) voltage output in a recognized grouping, corresponding to the location of the magnetic target 205. In one embodiment, a processor can analyze the output of the sensor having the highest voltage output and a predetermined number of sensor(s) to each side. The analog outputs of the sensors can be converted to digital output according to known methodology that can then be evaluated to determine the target location.

Other methods can also be used to determine a set of sensors to evaluate for position. One such method is correlation. In this method, a vector of values corresponding to the desired signal can be mathematically correlated against the vector signal set from scanned sensors 201. A peak in the correlation signal can indicate the center of the desired sensor set to evaluate.

Of course, the detection system need not utilize the peak signal and adjacent Hall sensors, but instead or in addition, sensors can evaluate the zero crossing signal that can result from using combinations of north and south magnets.

Referring again to FIG. 1A, the magnetic target 205 can be mounted at the base of syringe 207 in conjunction with probe 254. The magnetic target 205 can be mounted on a base plate of magnetically permeable material. By incorporating a base plate of magnetically permeable material beneath the magnetic target 205, the magnetic flux lines can be concentrated in a direction away from the base plate. Except at very close range, the greatest magnetic flux density can be present at the center of the magnet and extend perpendicular thereto, e.g., parallel to post 204 in the X direction. In general, the flux density decreases as a near Gaussian distribution function as one proceeds away from the magnet center line in the plane of the magnet. The field decreases in a near hyperbolic function as one proceeds away in a direction perpendicular to the magnet face. More details concerning suitable magnet assemblies are described in U.S. Pat. Nos. 5,285,154 and 5,351,004, both of which are incorporated herein by reference.

While the general construction shown in FIG. 1A can be used, it should not be considered to be limiting. In this particular embodiment, the target incorporates a magnet, with a magnetic field having a flux density which has a maximum at or adjacent to the center of the magnet and which decreases as a function of the distance moved away from the magnet. A single thin magnet can be used, or an array of magnets located side by side. The magnet or array of magnets then can be mounted in conjunction with a probe 254.

The magnetic material of target 205 can be any suitable material that has a high enough energy to be detectable over the distance between the target 205 and the sensors 201. A non-limiting list of suitable materials can include, without limitation, samarium cobalt, neodymium, or iron boron.

In one embodiment, a row of sensors 201, e.g., sensors of Hall effect transducers, can be placed side by side in a single row in the X direction along the post 204, as illustrated in FIG. 1C. In one preferred embodiment, the sensors 201 can be located close to each other. However, the distance between adjacent sensors can be affected by connection pins, casings, housings in which they are mounted, etc. For example, a small sensing component can be mounted in conjunction with pins or contacts that project from a housing for connection to a supply voltage, ground and output, respectively. Thus, even if housings are placed end to end with their pins projecting in the same or alternate directions, there will be a certain center to center distance between adjacent sensors. This distance can be reduced by providing an array of sensors that are canted at an angle to the sensing or X direction, and are provided in two rows with the sensors staggered relative to each other, as illustrated in FIG. 1B. This can decrease the center to center distance between adjacent sensing components for increased accuracy of a detector. Of course, other arrangements of the individual sensors 201 forming an array along post 204 are likewise encompassed in the present disclosure.

The Hall effect sensors can operate at a typical supply voltage of about 5 volts. The sensors can be designed to provide a known output voltage, e.g., about 2.5 volts, in the absence of a detectable magnetic field. The presence of a south pole magnetic field will increase the output voltage above the output voltage by an amount proportional to the magnetic field applied within a predetermined range of magnetic field strength. Conversely, the application of a north pole magnetic field will decrease the output voltage from its quiescent value proportional to the magnetic field applied. Thus, for a given sensor, the output voltage can be directly correlated to the magnetic field strength. Moreover, as the magnetic field strength decreases with distance from the magnet, the output voltage of a sensor can be directly correlated to the distance between the sensor and the magnet.

According to one embodiment, all of the sensors 201 can be mounted on a single printed circuit board. The printed circuit board also can include multiplexers for scanning of the outputs of the sensors. For example, in the case of 64 sensors, eight eight-port multiplexers can be used and coupled to a processor. A ninth multiplexer can be used to take the output of the eight multiplexers to one output for an analog-to-digital converter.

Each multiplexer can receive the outputs from eight of the Hall effect sensors and can provide a selected output on a line to a processor. The processor can include an analog-to-digital converter that, in combination with the multiplexers, scans the outputs of the sensors and converts the signals to digital form. The processing unit can also store an algorithm by which the Hall array outputs (i.e., the location of the target) can be processed to determine the location of the tip of the probe relative to the sensor having the reading that locates that particular sensor closest to the center of the magnetic target 205, for example, the sensor closest to the center of magnetic target can be the sensor obtaining the highest voltage output reading.

In one embodiment, processing of the outputs of the sensors 201 is accomplished by scanning all sensor outputs and determining which of them has the highest value. For this purpose, highest means the maximum difference from the quiescent value, i.e., the degree to which the output voltage has been shifted up or down from the quiescent voltage of, e.g., 2.5 volts. Highest value can also refer to the point in the array where a predetermined signal vector produces the highest correlation against the scanned sensors. The outputs of a predetermined number of sensors at each side of the highest signal can also be considered, such as three sensors at each side or four sensors at each side. The outputs of the remaining sensors can be ignored or can be incorporated, as desired. This predetermined number of outputs can then be used to calculate the location of the magnetic target 205 and also the tip of the probe 254 that is a known distance from the magnetic target 205. The accuracy of the measurement in the X direction can be maximized according any suitable methodology. For instance, the geometric arrangement of the sensors can be optimized, as discussed above, to limit the space between adjacent sensors, and the processor algorithm or algorithms used to convert the input signals to distance measurement can be adjusted to reflect the highest voltage output from any individual sensor depending upon its geometric location in the array and with respect to the magnetic target at its closest proximity.

Input information provided to a processing unit can include information concerning the position of each individual sensor. This can be by sensor number, for example, "1," "2," . . . , "64" for a 64-sensor array, which then can be converted to a location value based on the position of that sensor along the length of the post 204. One simple algorithm for calculating the position of the probe tip from the selected outputs is represented as follows: The sensor having the highest output is labeled "5," and the system is designed to consider the outputs of three sensors at each side. Accordingly, such additional sensors can be labeled S−3, S−2, S−1, S+1, S+2 and S+3. The sensor number can be multiplied by its respective output, and the mean value determined for the selected sensors. This value then can be converted to a distance or location value for the tip of the probe, as the processing unit can include as input data the distance from the target magnetic material 205 to the probe tip. Similarly, if the conversion of sensor number to location already has been made, the location is weighted by the output of the corresponding sensor, and the mean value determined and used as the indication of the location of the probe tip.

However, the above method assumes linear proportionality in variation of magnetic field strength away from the target in the sensing direction. In actuality, the variation is nonlinear, and more nearly a Gaussian distribution. Consequently, a more accurate result can be obtained by fitting the selected data to a nonlinear function such as a Gaussian distribution curve. In this computation, one of the parameters is the mean of the Gaussian fit, which can correspond to the target location. Commercially available software can be used to calculate an appropriate Gaussian distribution fit, such as TableCurve 2D, available from SPSS Inc. Thus, the algorithm can include the step of calculating the Gaussian distribution fit and determining the mean.

Other parameters of a Gaussian distribution that can be taken into account can include the spread of the Gaussian signal and the amplitude. Spread calculations can be used for error correction or fault detection. If a given sensor or sensors influence the fit of a distribution curve beyond reasonable parameters, that sensor or sensors can be assumed to be providing erroneous data and be ignored.

Approximate Gaussian distributions can be calculated with as few as three sensors, i.e., a maximum strength sensor and one at each side. Using greater numbers of sensors to perform the calculation can increase accuracy, and can also allow more flexibility in ignoring sensors whose values vary unreasonably from other sensors in the calculation set, for error correction and fault detection purposes.

Signals from the sensors 201 can create a data stream which can be sent to a processor. A processing unit can be internal or external to an ultrasound device 200. For example, data from sensors can be sent to a standard lap top or desk top computer processor or part of a self-contained ultrasound device as is known in the art. A processor can be loaded with suitable recognition and analysis software and can receive and analyze the stream of data from sensors.

The analysis of data carried out by the processor and associated determination of probe tip location and formation of the virtual probe image can be improved by taking into account variations from an ideal system. For instance, each ultrasound device can vary somewhat from ideal in placement and output of individual sensors used in a sensor array. This potential effect can be mitigated through determination of a voltage offset value for each sensor, and the inclusion of that value in the processor programming, such that the data obtained from each sensor is processed in conjunction with the voltage offset value for that sensor.

For instance, each sensor can be scanned in the absence of a magnetic field, and the amount of voltage offset, if any, can be determined for each sensor. This voltage offset value can take into account both any innate variation in output of the sensor as well as any variation due to slight mislocation of a sensor when being placed on an ultrasound device during manufacturing. The calculation of the position of the magnetic target along the sensor array can include the adjustment of a sensor output by its offset amount.

Other variations in individual ultrasound devices due to manufacturing can be accounted for as well through determination of offset values that can be programmed into the processor. For instance, and with reference to FIG. 1A, the distance from the surface 108 to the probe guide exit at the top of base 206 and the location of the sensor array with reference to the probe guide can vary slightly from one ultrasound device to another. This can be accounted for by including a value in the processor programming that represents this variation. $S_{offs}$ is utilized in the present disclosure to represent this variation. It includes two parts: one part is defined by the geometry of the ultrasound device and is the distance from the skin contacting surface of the device 108 at the exit of probe guide 126 to the beginning of the sensor array 103 (i.e., the farthest point of the sensor array from the base). The other component is dependant upon the manufacturing precision: how accurate the sensor array was placed on the ultrasound device in relation to the surface of the ultrasound transducer. This component is variable and will be different for every manufactured probe, but this difference is very small. This value can be obtained by a calibration process and can be provided to the processor programming algorithm.

An ultrasound device can also be programmed to include more than one $S_{offs}$ value, depending upon the application. For instance, and as described further below, an ultrasound device can be utilized with a sterilizable shield, so as to be used in a sterile procedure. In this embodiment, a device 200 can be enclosed within a shield, which can alter the value of $S_{offs}$. Such variations can be easily accounted for, however, for instance, by providing a switch on the ultrasound device, which can provide the input value for $S_{offs}$ to the processor, e.g., when the switch is set for a sterile application, the value for $S_{offs}$ takes into account the use of a shield about the ultrasound device 200.

In addition to standard methods for improving accuracy of a system, as described above, a system can correct for shifts in the location determination that can be brought about due to the flexibility of a probe. By way of example, FIG. 2 illustrates the flexing of a probe 254 that could occur during use if, for instance, a user inadvertently pushes the syringe 207 away from post 204 during a procedure. As can be seen, this can cause the portion of the probe 254 above the probe guide to bend. As the probe is flexible, the probe will straighten within the probe guide and proceed to the subdermal site along the path defined by the probe guide. This flexibility of the probe during delivery can lead to sensor information provided to the processor that differs from when the probe is aligned with the probe guide, which in turn can cause the processor to present a false location of exactly where the tip of the probe is on a sonogram.

Figure 3B:
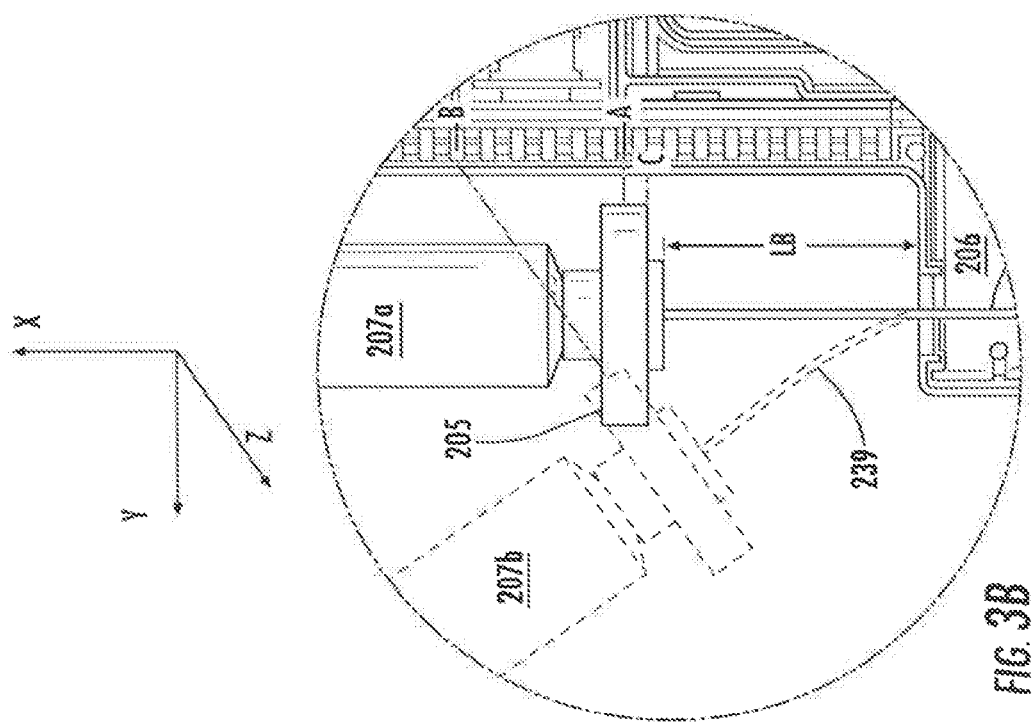
FIG. 3B illustrates a portion of FIG. 3A.
Figure 3A:
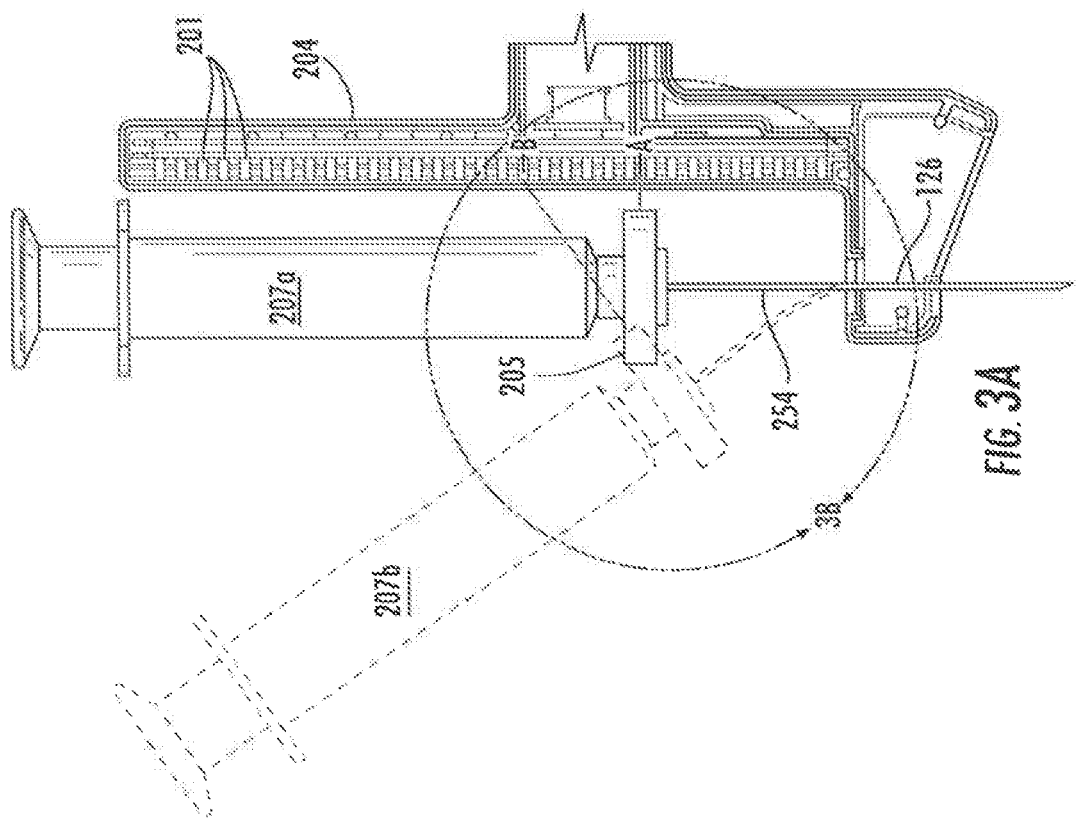
FIG. 3A illustrates an overlay of a FIGS. 1A and 2.

To better illustrate this condition, FIG. 3A overlays a probe 207a that is aligned with the probe guide 126 in the X direction and a probe 207b that has been pushed a distance out of alignment and is flexed away from post 204 above the probe guide 126. When the probe is in the position of 207a, the magnetic target 205 will be determined by the array of sensors 201 to be at the marked location A. However, when the probe is in the position of 207b, the array of sensors 201 will obtain a different view of the magnetic field, which can lead to the determination of the virtual probe tip at a point that differs from the location of the actual probe tip at the subdermal site. For instance, the highest magnetic field strength can be determined by the sensor array to be at B, rather than at A, when the probe is flexed. This can lead to an error in the correlation of the virtual probe image with the actual probe.

The probe tip location of the virtual image is determined by the processor based upon the combination of the location of the magnetic target as determined by the sensor array and the known distance between the magnetic target and the probe tip. Any flexing of the probe 254 does not affect the location of the actual subdermal probe tip, it merely tilts the magnet away from the post 204.

FIG. 3B illustrates in greater detail how the flexing of the probe can lead a system to locate a virtual probe tip at a location that varies from the location of the actual probe tip. This variation is affected by two distinct aspects. First, the magnetic field determination by the sensor array will locate that magnet at point B rather than at point A, as discussed. This will have the effect of placing the virtual probe tip above the actual probe tip (too shallow). In addition, the bending of the needle will alter the geometry of the system, i.e., the length $L_B$ is longer than the length of the chord 239 of the bent probe. The straight projection of the bent probe segment back to the sensor array will locate the magnet at point C, as shown in FIG. 3B, rather than at point A (where the magnet is located when the probe is not bent). This will have the effect of placing the virtual probe tip beneath the actual probe tip (too deep). Disclosed systems can take both of these affects in to account to accurately correlate a virtual image of a probe with the actual subdermal location of the probe.

The alteration in sensor reading that will occur when a probe is flexed out of alignment can be accounted for by the inclusion of a set of correlation factors into the processor algorithm. A set of correlation factors determined for a single ultrasound device can generally be applicable to all similar ultrasound devices (i.e., devices of a similar size and shape, a similar sensor array and location, etc.). Thus, a set of correlation factors need not be determined for every individual device (though this is certainly an optional embodiment). Rather, a set of correlation factors can be determined for a single type of device, and those correlation factors can then be incorporated in the processor algorithm for all ultrasound devices of a similar type.

To describe the determination of the correlation factors, certain terminology is utilized herein including:

$L_B$—Length of the bent portion of the probe (e.g., a needle).

$S_O$—The location of the magnetic target as would be determined by the sensor array were the probe to be properly aligned with the probe guide along the X axis.

$S_H$—The location of the magnetic target as determined by the sensor array when the probe is flexed out of this alignment.

$L_C$—The length of the probe guide as measured from the base surface of the probe guide 108 to the top exit from the probe guide (where the probe begins to be bent out of alignment).

$S_{offs}$—The calibrated distance from the skin contacting surface of an ultrasound device to the distal end of the sensor array.

H—A level index that represents the number of defined steps (or levels) out of alignment the probe is flexed. The level index H can be in any direction from the detector, i.e., in the Y axis, the Z axis or some combination thereof.

An equation to describe the correlation of a flexed probe has been determined to be:

$$S_O = S_H + (a*H+c)L_B + b*H + d$$

where $S_O$, $S_H$, H, and $L_B$ are as described above and a, b, c, and d are a set of correlation factors determined experimentally for each type of ultrasound device, an example of which is explained in further detail below.

This general equation has been determined experimentally by a best fit process, as described below. Beneficially, this equation can hold for any ultrasound device in which a probe that is ideally aligned with a probe guide and an ultrasound transducer as described herein can be bent out of alignment such that a portion of the probe is bent away from the detector. To accurately portray the location of the virtual probe tip on a formed image so that it is aligned with the actual subdermal location of the probe tip, this equation can be utilized by the processor software to correlate the measured value of $S_H$ with an aligned value $S_O$.

The number of correlation factors encompassed in the equation and programmed into the processor can vary, as desired, with the utilization of more correlation factors providing a higher correlation between the virtual image and the actual location of a subdermal probe. For instance, in one embodiment, fewer correlation factors can be utilized, and the processor instructions can include solving the equation $$S_O = S_H + a*H*L_B + b*H.$$

which incorporates only the a and b correlation factors. Similarly, the correlation equation can utilize only the a or the a, b, and c correlation factors in an equation. Moreover, additional factors can be incorporated in an equation, as would be known to one of skill in the art, with a improved alignment possible between the virtual probe tip and the actual probe tip when utilizing more correlation factors in the equation.

The values for $S_H$ and H can be obtained from the sensor during use. Specifically, $S_H$ is the value obtained by the sensor for the magnetic target location, and H can be obtained by the variation in the measured parameter (e.g., voltage) from the expected value when the probe is not bent. For instance, when the probe is not bent, and H=0, the voltage value obtained by the sensor at the magnetic target location will match the expected value. When the probe is flexed out of alignment, however, the highest voltage level obtained by the sensor can be less than expected. It is a simple matter to equate this drop in voltage with a level index value H, which can then be utilized in the correlation determination.

The value of $L_B$ is not directly obtainable by the sensor readings, as are $S_H$ and H. However, the length $L_B$ can be written in terms that are obtainable by the sensor reading. Specifically $$L_B = (S_{offs} - S_H) - L_C$$

By substituting this equation into the equation for determining $S_O$, a value for $S_O$ can be obtained in terms of parameters that are either predetermined for each ultrasound device (e.g., $L_C$, $S_{offs}$) or determinable from the sensor reading ($S_H$, H).

Specific values for the correlation factors a, b, c, d, can be experimentally determined, as described in the examples section below. For example, the correlation factors can be:

a—between about −0.045 and about −0.055, for instance about −0.050;

b—0 or between about 4 and about 5, for instance about 4.30;

c—0 or between about 0.02 and about 0.03, for instance about 0.028;

d—0 or between about −0.5 and about −0.06, for instance about −0.053.

The correlation equation can be included in the instruction provided to the processor in the form of software, and the location of a virtual probe tip imaged in conjunction with a sonogram can be correlated with the location of an actual subdermal probe tip.

Upon determination of a value for H from the readings obtained by the sensor, the distance the target magnet has traveled away from alignment can be determined. In one embodiment, a device can include a warning signal to alert a user should the magnet be moved beyond a predetermined level. For instance, should a probe be flexed such that the level index H becomes greater than, e.g., 5 or 6, an alarm can be triggered by the processor, so as to alert a user that the probe has been moved out of the desired position. An alarm can be visual, auditory, tactile, or any combination thereof. For instance, a signal light can be turned on should the level index determined at the processor exceed a predetermined value.

Figure 4A:
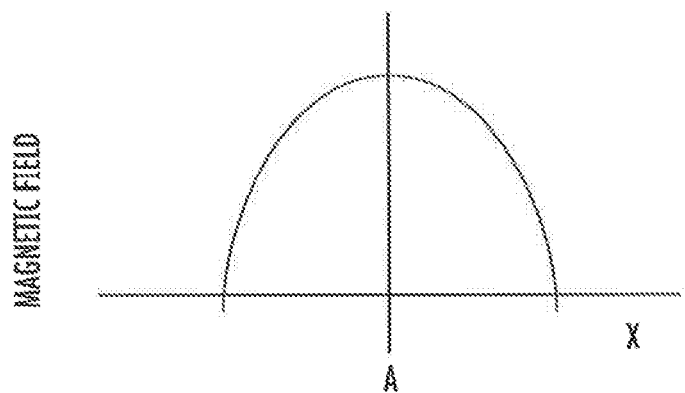
FIGS. 4A and 4B graphically illustrate the change in the magnetic field strength along a sensor array for an aligned probe (FIG. 4A) and a probe that is flexed out of alignment (FIG. 4B)
Figure 4B:
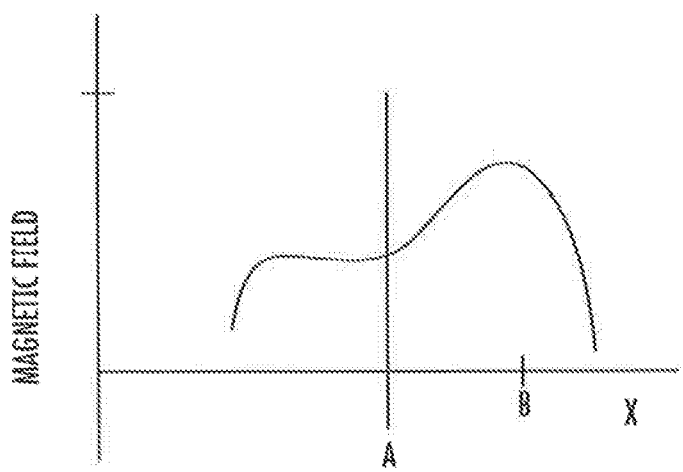

According to another embodiment, correlation of the virtual probe location as determined by the motion detector with the actual probe location can be determined through examination of the individual sensor outputs. As previously discussed, in one embodiment, a plurality of sensors are examined for determination of the location of the magnetic target. Specifically, a number of sensors both above and below a central signal (i.e., that signal location corresponding to the magnet locus) can also be considered, such as three sensors at each side or four sensors at each side. With reference to FIG. 1A, when a probe is aligned with the probe guide opening along the X-axis and generally parallel to the array of sensors 201 in post 204, the variation of magnetic field strength in the sensors above and below the target will be known, and in one embodiment, can be generally equivalent to each other (see, e.g., FIG. 4A, which illustrates one embodiment of the magnetic field strength along the X-axis, with the magnet at point A). For instance, the magnetic field strength can decrease according to a Gaussian distribution in both directions from the highest signal at the center sensor to the individual sensors that are farther away from the highest signal strength. Even if the decrease above and below the highest signal strength is not equivalent, the ideal decrease in both directions can be known. Upon flexing of a probe away from the desired alignment, the magnetic field strength variation will be altered from the ideal distribution as the magnet and the magnetic field become tipped as compared to the sensors, as shown in FIG. 4B. Thus, this distribution curve and the variation from ideal of the magnetic field distribution curve can be utilized in another embodiment to determine the amount of flex from the aligned position of a probe.

Figure 5C:
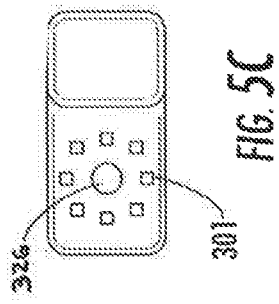
FIG. 5C illustrates a top view of another embodiment of an array of sensors on the base of an ultrasound device.
Figure 5B:
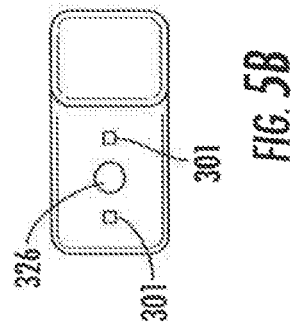
FIG. 5B illustrates a top view of the ultrasound device of FIG. 5A.
Figure 5A:
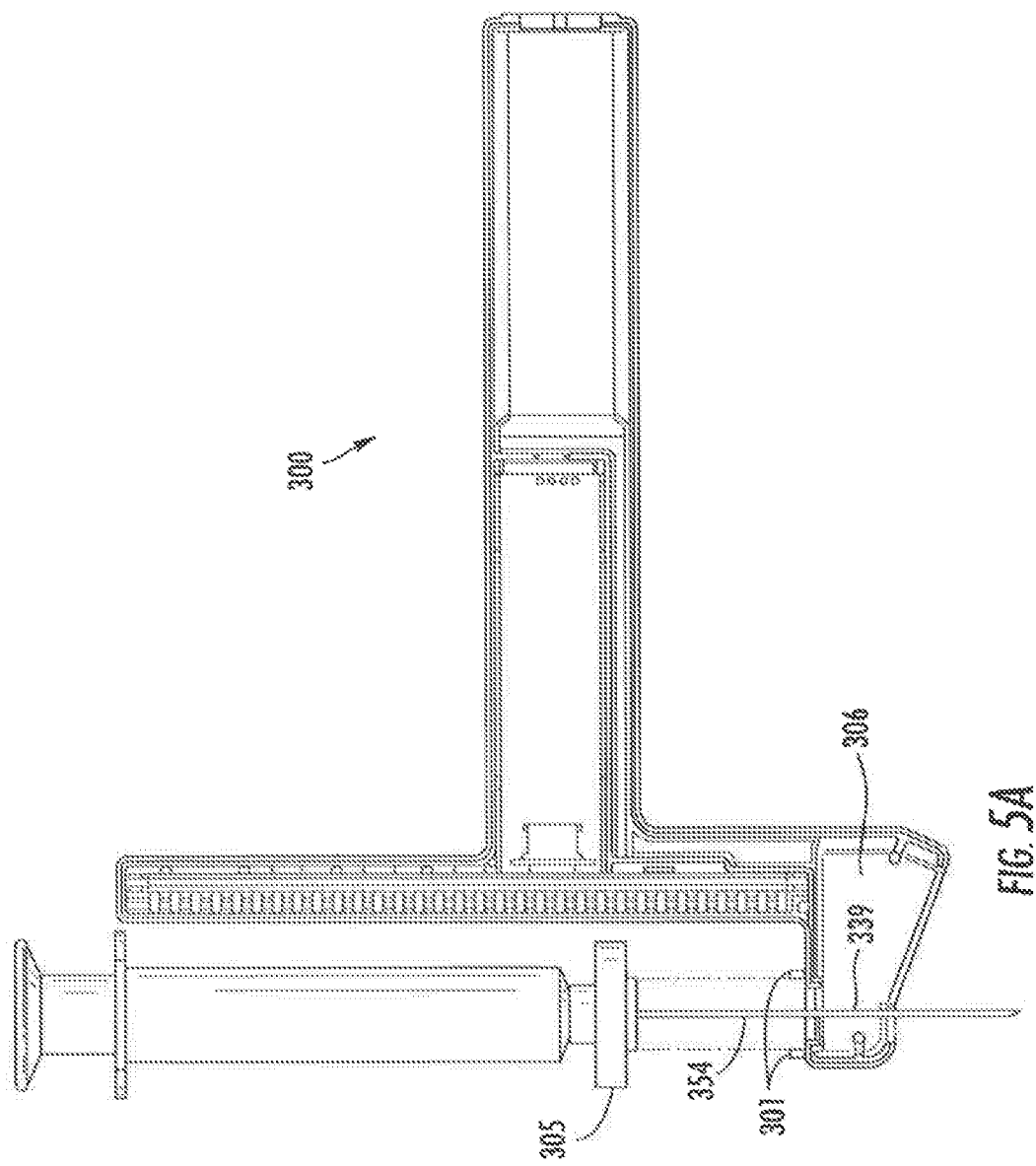
FIG. 5A illustrates an ultrasound device including a series of sensors on the base of the ultrasound device.

While the above description is specific for magnetic sensors located on the post of a device, it should be understood that the present disclosure is not limited to this specific sensor type. Any other type of sensor can be utilized in disclosed ultrasound devices. For instance, FIG. 5A illustrates sensors 301 located on the base 306 of ultrasound device 300. Sensors 301 can be on the surface of base 306 or within the base 306, depending upon the sensor type, the materials of the base 306 and so forth. Sensors 301 are directed toward a target 305 associated with probe 354. Sensors 301 can utilize any suitable format, e.g., optics, sonics, proximity sensors, magnetics, etc., and determine the distance from the sensors 301 to the target 305. Input data to a processor can include the distance from the target 305 to the tip of probe 354 so as to accurately portray the location of the actual probe in forming a virtual probe image.

Figure 6:
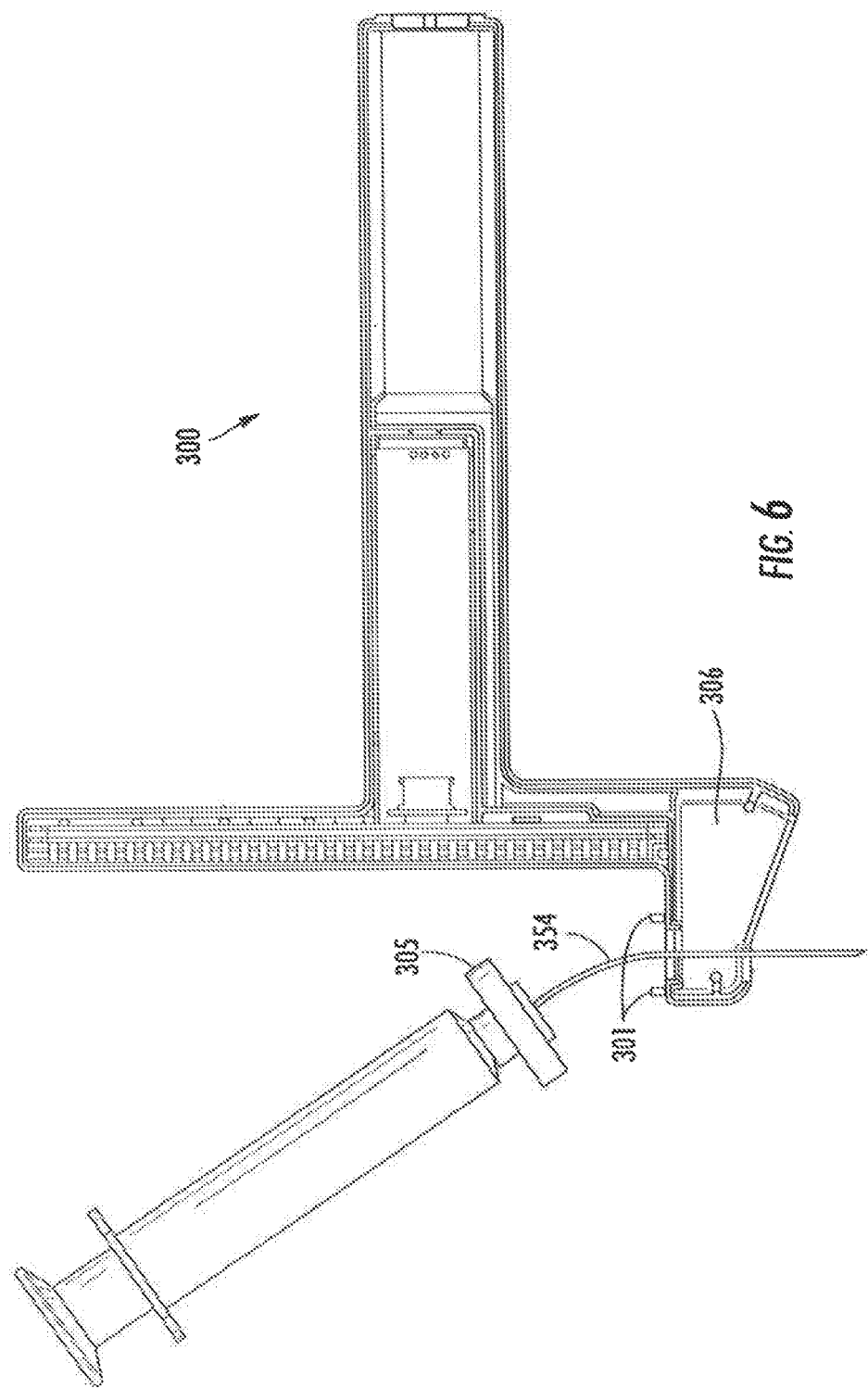
FIG. 6 illustrates the ultrasound device of FIG. 5A upon deformation of a probe during use.

When the probe 354 is aligned with the probe guide opening 339 and centered above the probe guide opening, as illustrated in FIG. 5A, the two sensors 301 will obtain equivalent distances. FIG. 5B illustrates a top view of the device including two sensors illustrated in FIG. 5A. As can be seen, ultrasound device 300 includes two sensors 301 radially opposite one another across the probe guide opening 326. Upon flexing of the upper portion of a probe 354, as shown in FIG. 6, the distance measured from one sensor will differ from that of its counterpart that is opposite across the probe guide opening, as shown. Thus, the processor can obtain data and determine that the distance from each sensor to the target is no longer equivalent, as it should be.

According to this embodiment, the processor can include a correlation algorithm, similar to that described above for a sensor array located on a post parallel to the aligned direction of probe travel, so as to accurately locate the tip of the virtual probe image. For instance, an $S_{offs}$, as described above can be obtained for each device, based upon the variations in manufacturing between devices, and the measured sensor array result for the location of the target, $S_H$, can be corrected to provide $S_0$, i.e., what that result would be if the probe 354 were not flexed out of the aligned position. A series of correlation factors experimentally determined for an ultrasound device can be programmed into the processor for application to all devices of that same type. In other words, the correlation factors obtained can be a permanent part of the processor, and each processor need not be specifically reprogrammed for every device.

An ultrasound device can include a plurality of sensors at the base. For instance, FIG. 5C illustrates a top view of an embodiment in which an ultrasound device includes multiple sensors 301 surrounding a probe guide opening 329. When a probe is aligned with the probe guide opening in the X direction, all of the sensors will have an essentially identical reading as to distance from the sensor to the target. If the target is pushed in any direction and thus out of alignment, the sensors will register the target at a variety of different distances, alerting the processor to the misalignment. The correction algorithm can be similar to that described above for a two-sensor system, but can incorporate additional parameters for the other sensors.

A processing unit can also include standard imaging software as is generally known in the art to receive data from an ultrasound transducer that is a part of the ultrasound device in addition to software that can process readings from a detector with regard to misalignment of a probe in the device, as described, and form a virtual image on a monitor that accurately portrays the location of the actual probe being inserted subdermally. Input data for the processor, such as the length of the probe, offset values, correlation factors, and so forth, can be entered into the processor by the user at the time of use or can be preprogrammed into the system as default data, depending upon the nature of the data, as discussed. Through analysis of the data stream received from both the detector and the ultrasound transducer, a processor can calculate the position of the probe tip relative to the ultrasound transducer, relative to a sensor, relative to the skin contacting surface of the device, or relative to any other convenient reference point. A processor can communicate this position information digitally to a monitor and the information can be displayed on the monitor such as in a numerical format or as a real time image of a virtual probe. Moreover, this data can be illustrated in conjunction with, e.g., overlaid on, the sonogram that displays an image of the subdermal site, such as a blood vessel.

In such a manner, disclosed ultrasound devices can be utilized to actually show the approach of a probe toward a subdermal site on a monitor throughout the entire procedure. In addition, disclosed devices can be utilized to ensure the probe tip remains at the subdermal site during subsequent procedures. For example, as long as the detector is interacting with the target the virtual image of the probe can remain on the monitor. Thus, any motion of the probe tip in relation to the subdermal site can be noted by an observer, even following the clamping of the probe within the probe guide.

Any type of ultrasound transducer as is generally known in the art can be incorporated in ultrasound devices as disclosed herein. By way of example, a piezoelectric transducer formed of one or more piezoelectric crystalline materials arranged in a two or three-dimensional array can be utilized. Such materials generally include ferroelectric piezoceramic crystalline materials such as lead zirconate titanate (PZT). In one embodiment, the elements that form the array can be individual electrode or electrode segments mounted on a single piezoelectric substrate, such as those described in U.S. Pat. No. 5,291,090 to Dias, which is incorporated herein by reference thereto.

In general, an ultrasound transducer can be formed of multiple elements. However, single crystal ultrasound transducers are also encompassed by the present disclosure. The use of a multiple element ultrasound transducer can be advantageous in certain embodiments, as the individual elements that make up the transducer array can be controlled so as to limit or prevent any break or edge effects in a sonogram. For instance, the firing sequence of individual crystals can be manipulated through various control systems and prevent any possible 'blind spots' in a sonogram as well as to clarify the edges of individual biological structures in the sonogram. Such control systems are generally known in the art and thus will not be described in detail.

Referring again to FIG. 1A, the scanned plane (i.e., the plane of the sonogram) can be the geometric central plane of the beam transmitted from the ultrasound transducer 110. In one preferred embodiment, the path of a probe that is guided through probe guide opening 126 can be within the scanned plane. This is not a requirement of the present disclosure, however. For instance, the path of a probe passing through probe guide opening 126 can be at an angle to the scanned plane such that it intersects the scanned plane at a point. By way of example, the line defined by the path of a probe passing through the probe guide opening 126 can be at an angle of +1° to the scanned plane in one embodiment, at an angle of ±0.6 degrees in another embodiment, or at a lesser or greater angle in another embodiment. For instance, a line defined by the path of a probe passing through the probe guide opening can be at an angle of ±10°, ±20°, ±45°, or even greater, in other embodiments.

An ultrasound device as encompassed herein can have any convenient geometry. For instance, and with reference to FIG. 1, handle 102 can be set at an angle to post 204 so as to be comfortably held in the hand while the device is being utilized. For instance, in the illustrated embodiment, handle 102 is about 90° to post 204, though this angle can be varied as desired. Moreover, in another embodiment described further herein, an ultrasound device need not include an extending handle portion at all.

The base 206 of an ultrasound device can also have any convenient geometry. For instance, the skin contacting surfaces 108 can be angled, as illustrated, or can be planar from edge to edge. When present, the angle of a skin contacting surface 108 can vary from 0° to about 30°, or from about 10° to about 20° in another embodiment. In yet another embodiment, a skin contact surface can define an angle opposite to that illustrated in FIG. 1, i.e., the skin contacting surface 108 can be convex. A skin contacting surface can also include curvature, e.g., can define an arcuate profile along the length or width of the surface. The footprint shape of the skin contacting surface 108 may be rectangular, round, oblong, triangular, etc. With regard to size, the skin contacting surface 108 can be, e.g., between about 0.5 inches and about 6 inches on its greatest length. In one embodiment, the skin contacting surface 108 can be about 0.5 inches on its greatest width and can promote stability of the device during use. In other embodiments, it can be larger, however, such as about 1 inch on its greatest width, about 2 inches on its greatest width, or even larger.

The shape of all or a portion of an ultrasound device may be particularly designed to fit specific locations of the anatomy. For example, a device may be shaped to be utilized specifically for infraclavicular approach to the subclavian vein, approach to the internal jugular vein, specific biopsy procedures including, without limitation, breast biopsy, thyroid nodule biopsy, prostate biopsy, lymph node biopsy, and so forth, or some other specific use. Variations in shape for any particular application can include, for example, a specific geometry for the footprint of a base, alteration in the size of post and/or handle, as well as variation in angles at which various elements of a device meet each other.

An ultrasound device can be utilized in conjunction with a sterilizable shield, for instance in those embodiments in which a probe is intended for use in a sterile field. A sterilizable shield can be formed of sterilizable materials as are generally known in the art. In one embodiment, a sterilizable shield can be formed of single-use materials such as polymeric materials, and the entire shield can be properly disposed of following a single use. In another embodiment, a sterilizable shield can be utilized multiple times, in which case it can be formed of a material that can be properly sterilized between uses. A sterilizable shield can be formed of a moldable thermoplastic or thermoset polymeric material including, without limitation, polyester, polyvinyl chloride, polycarbonate, and so forth.

Figure 7:
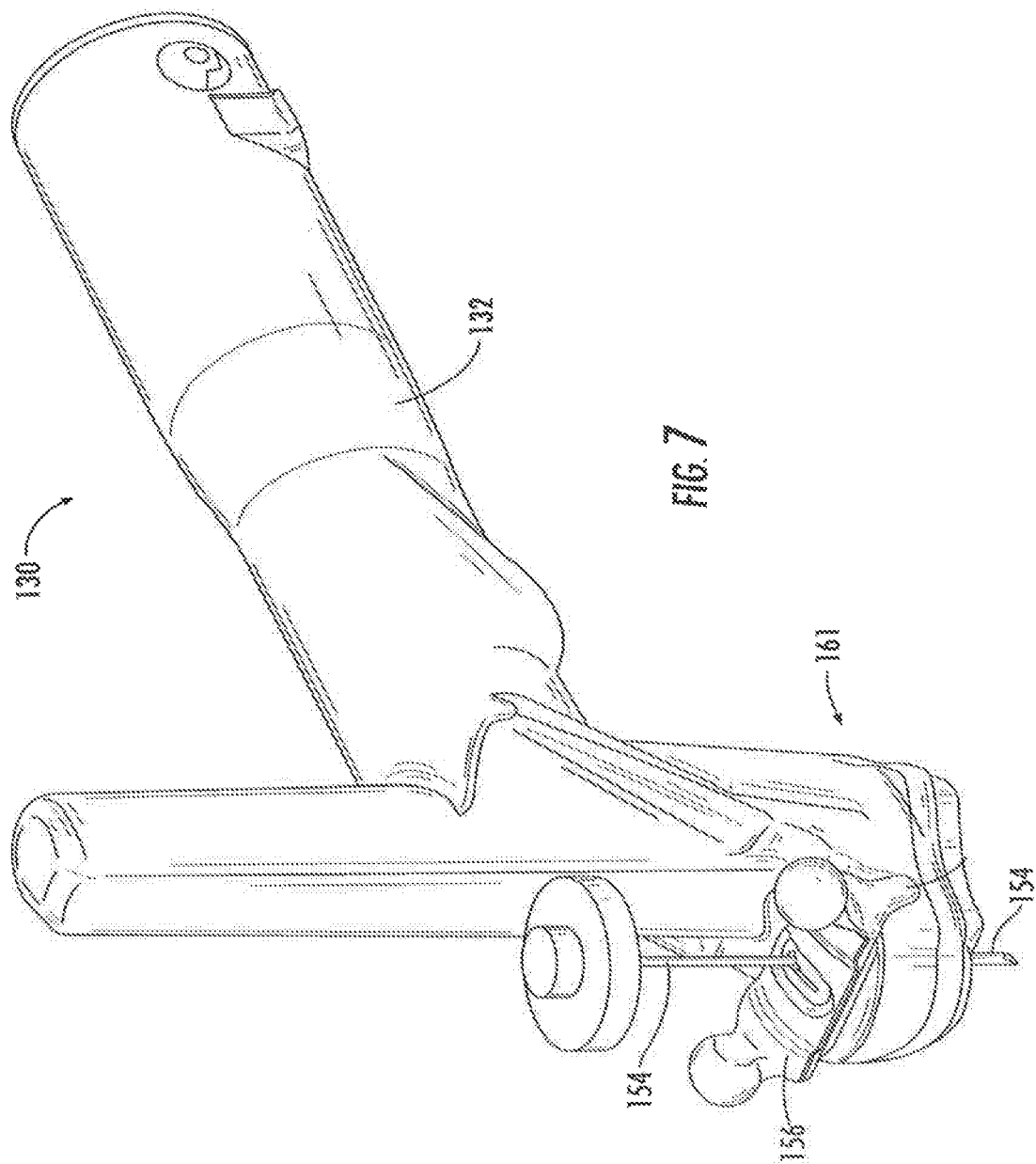
FIG. 7 illustrates a sterilizable shield that can encase an ultrasound device.

FIG. 7 illustrates one example of a sterilizable shield 130 as may be utilized to encase an ultrasound device. Sterilizable shield 130 can include a lower section 132, details of which are shown in FIG. 8, and an upper section 134, details of which are shown in FIG. 9.

Figure 8:
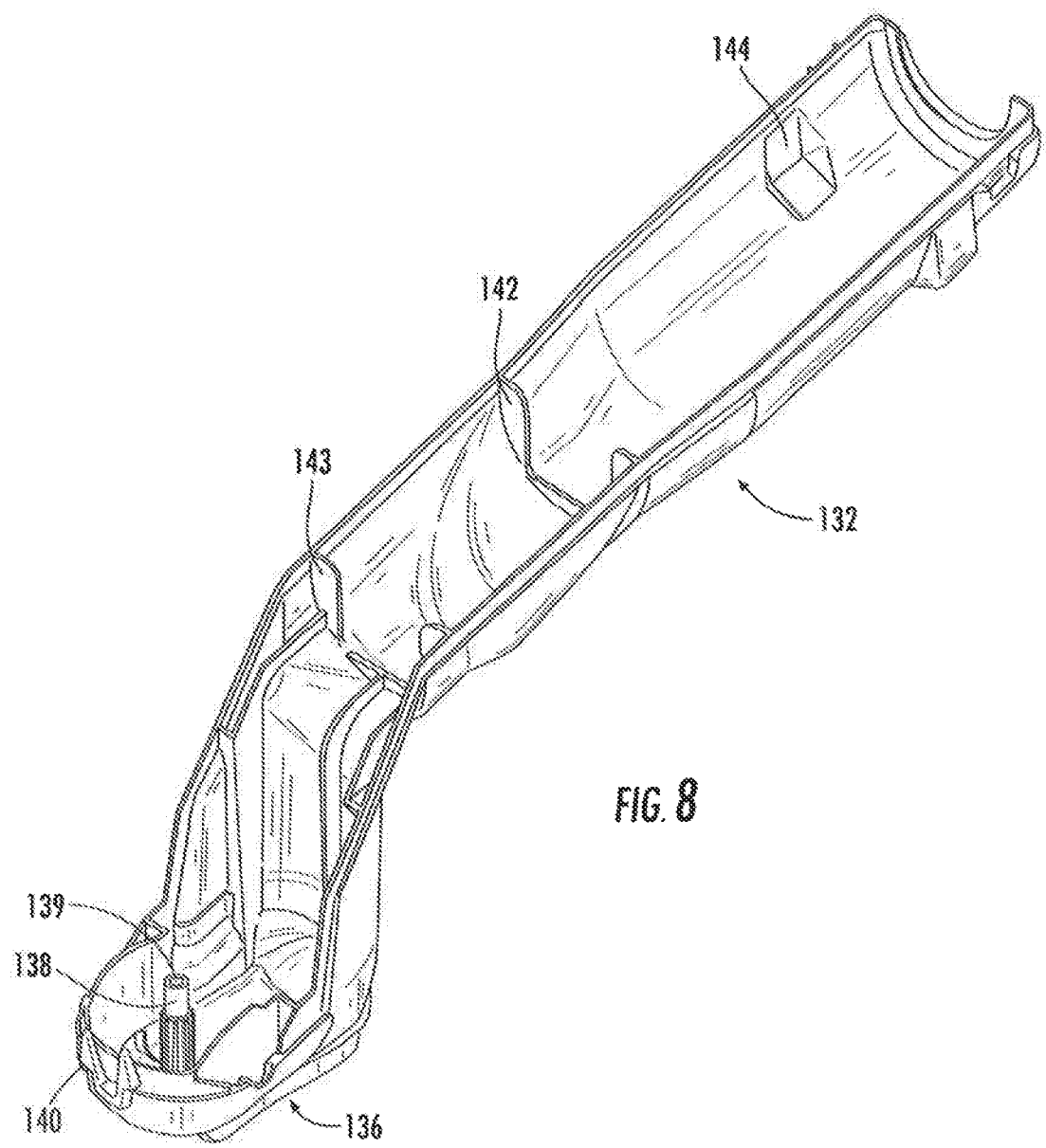
FIG. 8 illustrates the bottom portion of the sterilizable shield of FIG. 7.
Figure 9:
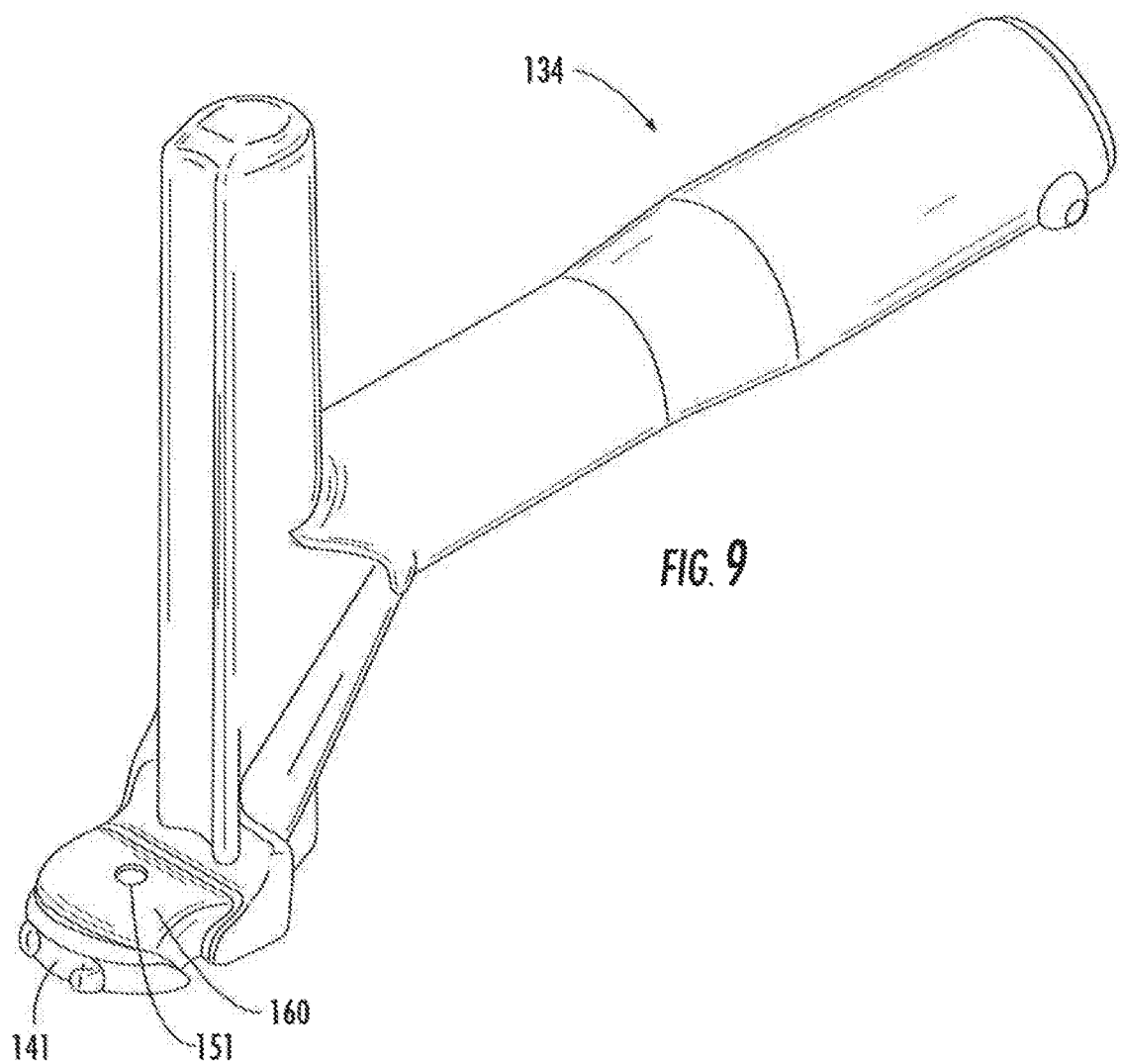
FIG. 9 illustrates the top portion of a sterilizable shield, the bottom portion of which is illustrated in FIG. 8.

With reference to FIG. 8, shield section 132 can include a base 136 formed of an ultrasonic transmissive material. Base 136 can be of any suitable size and shape, but formed such that an ultrasound transducer housing base may be seated firmly in shield base 136. Generally, a small amount of an ultrasonic gel can be placed between the bottom surface of the transducer housing base and shield base 136 during seating to prevent any air between the two and promote transmission of ultrasonic waves.

Arising out of shield base 136 is guide post 138. Guide post 138 defines at least a portion of a probe guide 139 therethrough. Probe guide 139 extends uninterrupted completely through both guide post 138 and shield base 136. Guide post 138 can include tabs as shown, or other formations such as hooks, insets, or the like that can be utilized to properly assemble shield base 136 about an ultrasound transducer housing. In one embodiment, guide post 138 may include a removable cap (not shown) for protection of the interior sterile surface of probe guide 139 during assembly of shield 130 with an ultrasound transducer housing. As shown in FIG. 9, section 134 defines the terminal portion 151 of probe guide 139. Terminal portion 151 is sized so as to snugly reside over the top of guide post 138 of section 132 and form uninterrupted probe guide 139 extending from the top surface of portion 160 of section 134 to the bottom surface of base 136 of section 132.

As can be seen, shield section 132 can also include tabs 140, 142, 143, 144, etc. that can be utilized in properly seating an ultrasound housing within shield section 132 as well as aligning shield section 132 with shield section 134 when assembling the complete shield 130 about an ultrasound transducer housing.

Tabs 140 on shield section 132 can match corresponding notches 141 on shield section 134 shown in FIG. 9. Together tabs 140 and notch 141 form a fastener that can secure shield section 132 and shield section 134 to one another. During assembly, tabs 140 can snap into notch 141 to securely fasten the two sections together and prevent separation of the sections 132, 134 during use. Of course, a shield can include additional fasteners at other locations between the two sections, or can include a single fastener at an alternative location, as would be known to one of skill in the art.

In order to disassemble shield 130, tabs 140 can be simply pinched together and slid out of notch 141. In another embodiment, a single-use fastening mechanism can be employed to secure sections of a sterilizable shield to one another. According to this embodiment, in order to disassemble a shield following use, the tabs of the fastener can be permanently disabled upon disassembly of the shield. For instance, tabs 140 and/or notch 141 can be permanently broken away from the shield by a pulling or twisting motion, allowing the shield sections to come apart and also ensuring that the shield, which is no longer sterile, cannot be utilized again. Any method that can ensure that a fastener can only be utilized a single time may alternatively be utilized.

To assemble the illustrated sterilizable ultrasound device, an ultrasound device 200 defining probe guide opening 126 shown in FIG. 1A can be seated in section 132 of sterilizable shield 130 such that guide post 138 extends through transducer housing probe guide opening 126. As probe guide opening 126 of ultrasound device 200 is slid over guide post 138, tabs on guide post 138 can slide or snap into recesses of probe guide opening 126 (not shown), helping to properly seat ultrasound device 200 in section 132. After ultrasound device 200 is seated in section 132, section 134 can be aligned with section 132 and fastened into place to cover the top of ultrasound device 200. If a protective cap covers the end of guide post 138, it can be removed during assembly and maintain the sterility of the interior of the probe guide 139 throughout the assembly process. Tabs 140 can snap or slide into recesses notch 141 to fasten and secure section 132 and 134 together.

Following the above described assembly process, probe guide 139 can extend continuously from the top of portion 160 of shield portion 134 through the shield base 136. Moreover, and of great benefit to the device, probe guide 139 can be sterile and within the probe guide opening 126 of ultrasound device 200.

Though illustrated as being formed of two separable sections, a sterilizable shield can be hinged or can include additional sections, as desired. For instance, a sterilizable shield can be formed of two, three, or more separable sections that can be assembled to enclose all or a part of an ultrasound housing and form a sterile barrier between the enclosed housing and an exterior field. In another embodiment, a sterilizable shield can be of a unitary construction. For instance, a sterilizable shield can be of a pliant material that can enclose all or a portion of an ultrasound housing and form a sterile barrier between the enclosed housing and an exterior field.

Referring to FIG. 7, the assembled sterilizable shield 130 can also include a clamp 156. During use, clamp 156 can firmly hold a probe 154 in the probe guide and prevent motion of the probe 154 during a procedure such as a catheter insertion, a biopsy procedure, fluid aspiration, or the like. Motion of the subdermal probe tip following insertion can be much less likely when the probe 154 is securely clamped to the probe guide of the sterilizable shield 130 and the ultrasound device is in turn held and stabilized by an operator as compared to devices in which a probe is simply held free-hand by an operator.

As can be seen in FIG. 7, a probe 154 can extend through a probe guide (not shown) of sterilizable shield 130. Clamp 156 sits atop the base 161 of sterilizable shield 130 such that probe 154 passes through clamp aperture 158 as shown. patent application Ser. No. 12/576,498 (now U.S. Pat. No. 8,496,592) to Ridley, et al., which is incorporated by reference, describes one clamp as may be incorporated with an ultrasound device. Any other clamping action can alternatively be utilized. For instance, a clamp can tighten about a probe by a rotational motion of a clamping surface about a clamp, as is illustrated in U.S. Pat. No. 7,244,234 to Ridley, et al., which is incorporated herein by reference. Any relative motion between a clamp and a probe that can serve to firmly hold a probe in place through a friction hold, through physical interaction of probe/clamp segments, or through any combination thereof is encompassed in the present disclosure.

Figure 10:
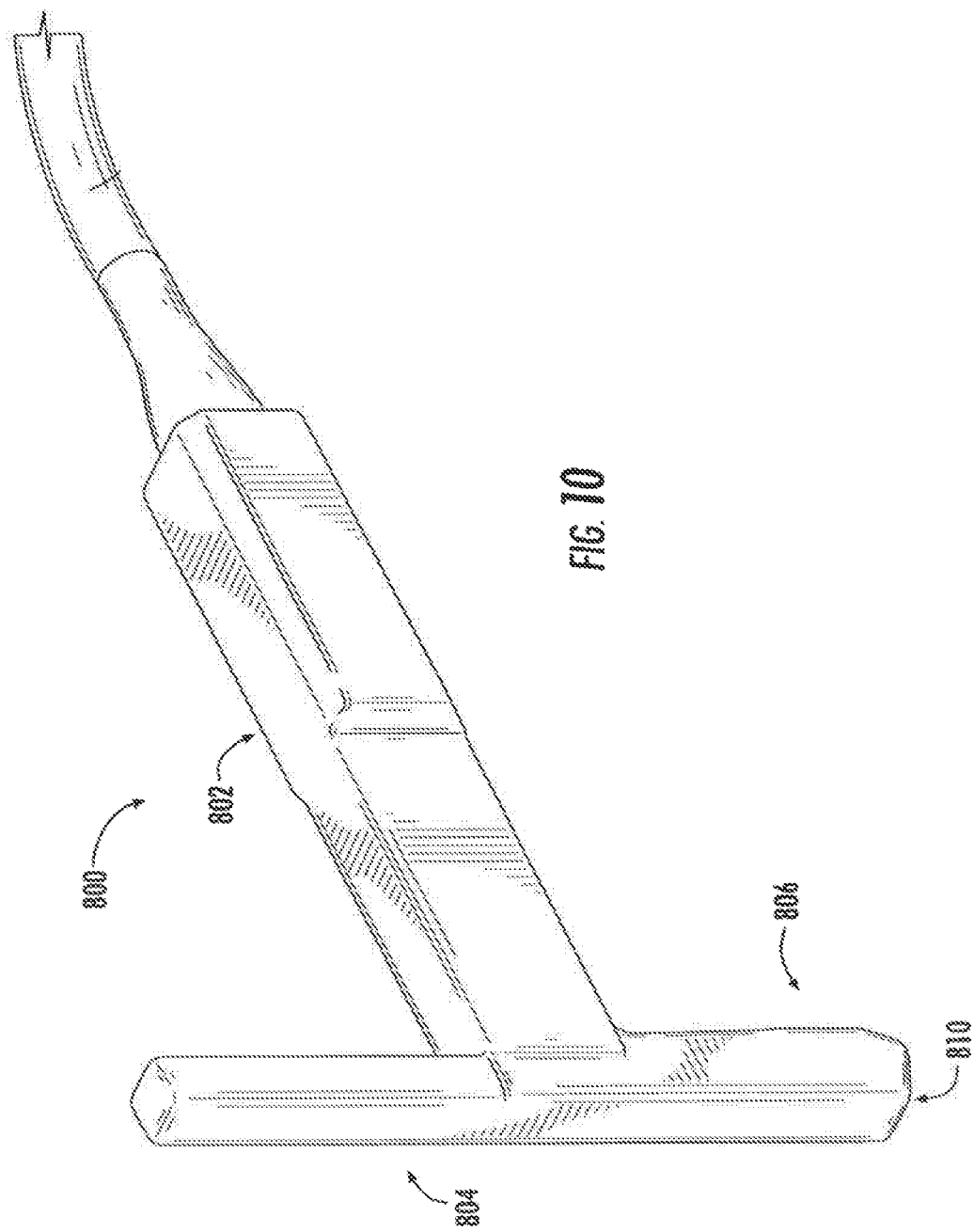
FIG. 10 illustrates another embodiment of an ultrasound device as disclosed herein.

FIG. 10 illustrates another embodiment of an ultrasound device 800 that is encompassed by the present disclosure. According to this embodiment, ultrasound device 800 can include a handle 802, a post 804, and a base 806. Ultrasound device 800 also defines a lower surface 810, as shown. In this particular embodiment, however, the ultrasound transducer housing does not include a probe guide opening. Instead, ultrasound device 800 is removably attachable to a second portion that defines the probe guide opening. For instance, ultrasound device 800 can be utilized in conjunction with a sterilizable shield that defines a probe guide. Moreover, the sterilizable shield can be formed of a single or multiple removably attachable pieces.

Figure 11:
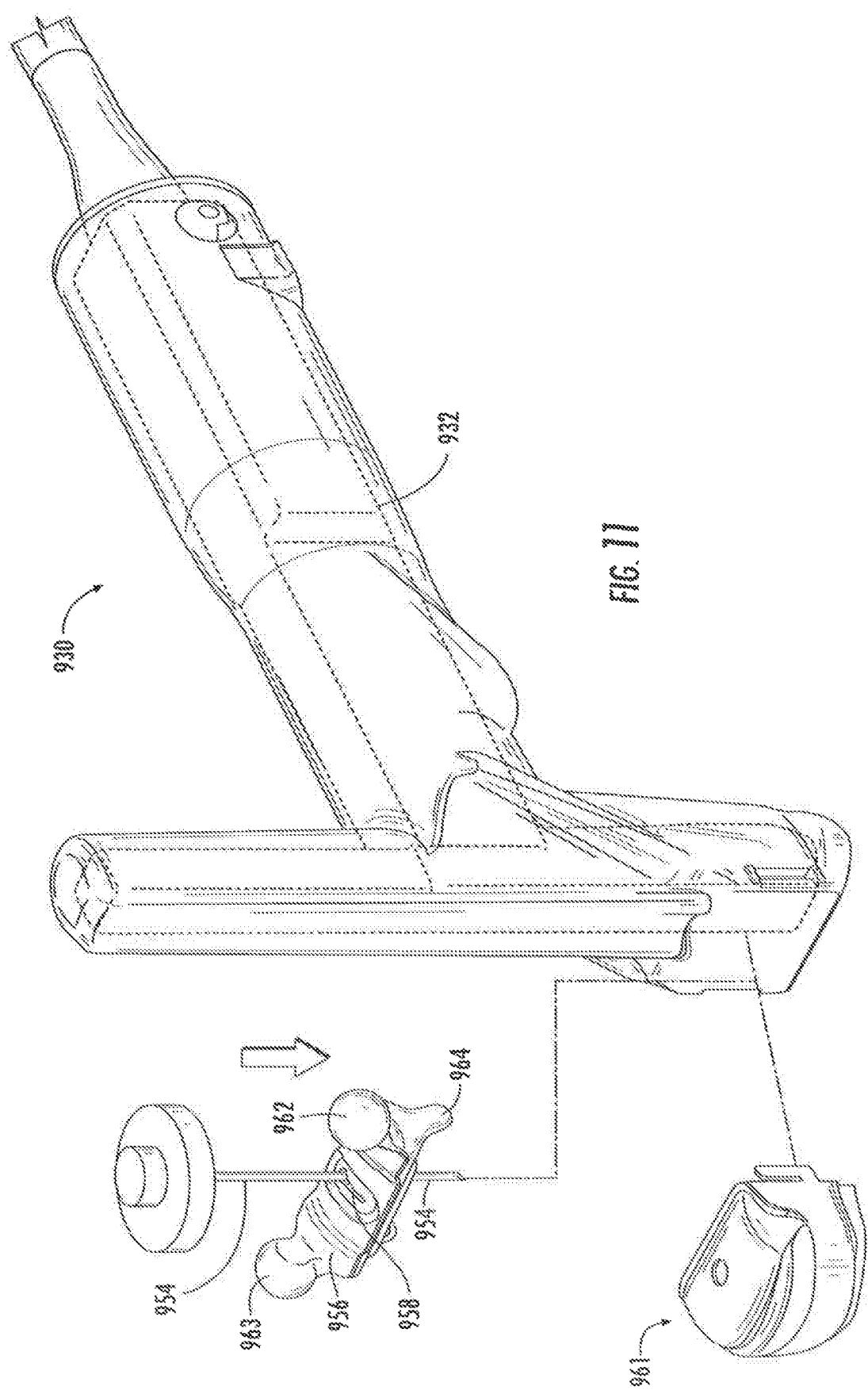
FIG. 11 illustrates a partially exploded version of a system including the ultrasound device as is illustrated in FIG. 10.

FIG. 11 illustrates a sterilizable shield 930 that can be used in conjunction with an ultrasound device 800 illustrated in FIG. 10. Sterilizable shield 930 includes section 932 and section 961, which defines a probe guide for passage of probe 954 therethrough. Additionally, section 932 can be separable into two or more section. Section 961 can also include clamp 956 defining aperture 958 and formations 962, 963. Clamp 956 can rotate about pivot 964 for clamping probe 954 in the probe guide. During use, section 961 can be attached to section 932, for instance by use of aligned tabs and notches, and so forth, so as to attach the probe guide portion to the sterilizable shield.

Of course, any other arrangement of the individual portions of an ultrasound device are encompassed within the present disclosure. For instance, in one embodiment, a section of an ultrasound device that does not define a probe guide opening, as illustrated in FIG. 10, can be removably attached to a section that defines the probe guide opening and includes the clamp, without enclosing the entire device in a sterilizable shield. In another embodiment, a sterilizable shield portion can cover only the skin contacting surface of an ultrasound device. For instance, a shield portion can snap onto the base of an ultrasound device.

Figure 12:
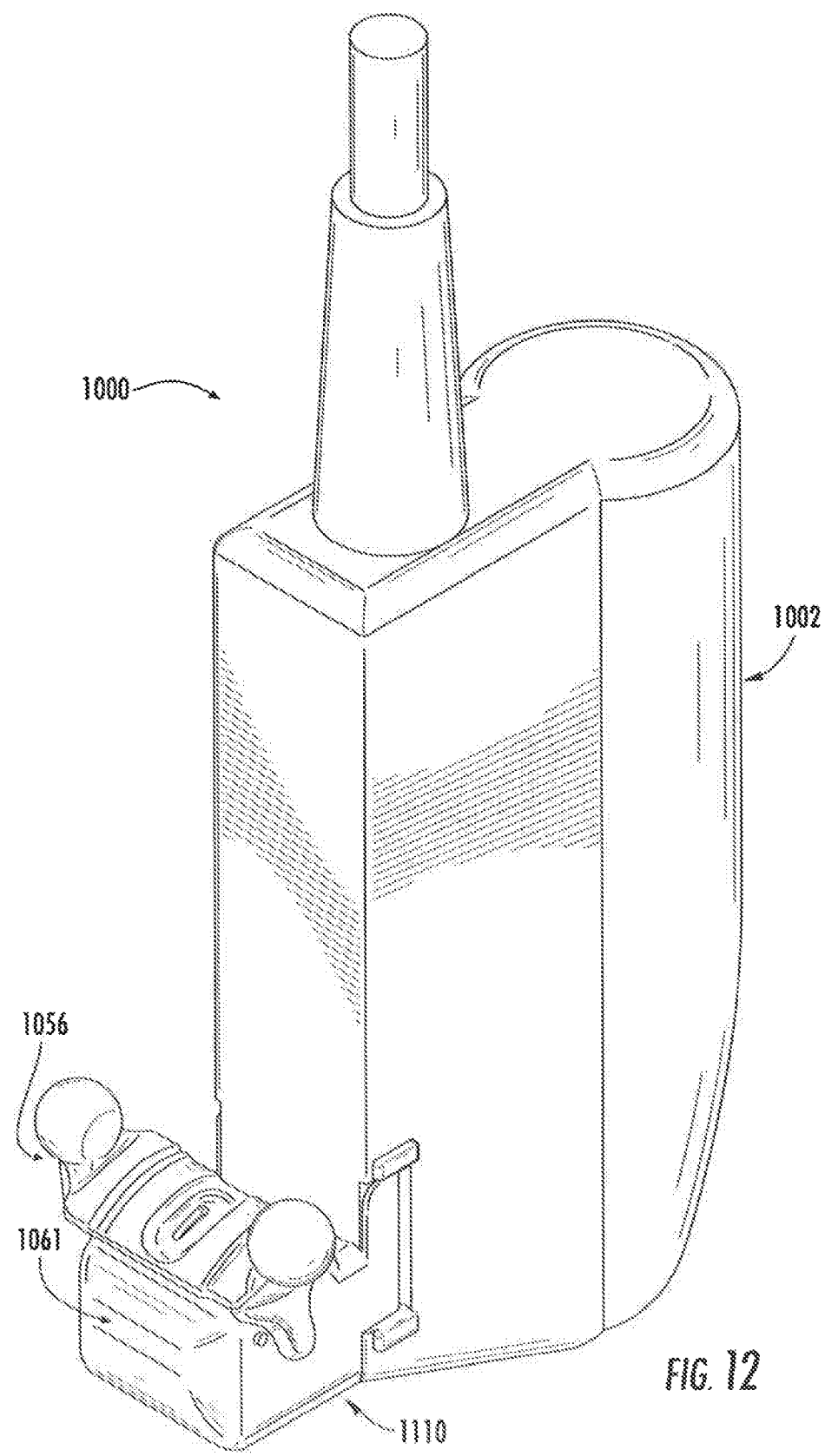
FIG. 12 illustrates another embodiment of an ultrasound device as disclosed herein.

Another embodiment of an ultrasound device is illustrated in FIG. 12. As can be seen, ultrasound device 1000 does not include a handle portion. Such a device can be comfortably held by the rounded back portion 1002, with the skin contacting surface 1110 held against a subject. Ultrasound device 1000 can include some form of attachment, e.g., tabs, slots, hooks, etc, to attach a probe guide portion 1061 comprising clamp 1056 to device 1000. When attached, the probe guide of portion 1061 can be aligned with an ultrasound transducer located in the base of ultrasound device 1000.

Presently disclosed ultrasound devices and methods may be utilized in many different medical procedures. Exemplary applications for the devices can include, without limitation Central Venous Catheterization
Cardiac Catheterization (Central Arterial Access)
Dialysis Catheter Placement
Breast Biopsies
Paracentesis
Pericardiocentesis
Thoracentesis
Arthrocentesis
Lumbar Puncture
Epidural Catheter Placement
Peripherally Inserted Central Catheter (PICC) line placement
Thyroid Nodule Biopsies
Cholecystic Drain Placement
Amniocentesis
Regional Anesthesia—Nerve Block Some of these exemplary procedures have employed the use of ultrasound devices in the past, and all of these procedures, as well as others not specifically listed, could utilize disclosed ultrasound devices to improve procedural safety as well as patient safety and comfort, in addition to provide more economical use of ultrasound devices.

The present disclosure may be better understood with reference to the Examples, provided below.

Example 1

Figure 13:
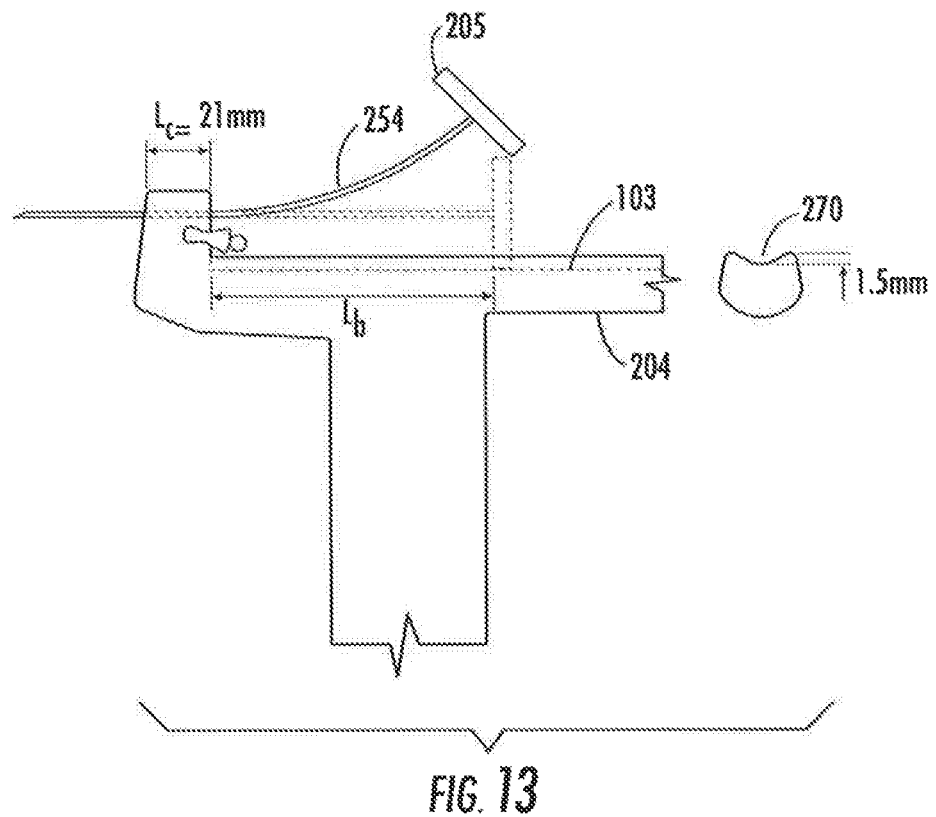
FIG. 13 illustrates a system as utilized in the Example, provided herein.

An ultrasound device as illustrated in FIG. 13 was utilized. The needle probe 254 was flexed away from the post 204 of the device, as shown. A sensor array 103 of Hall effect sensors was located within the post 204. The sensors used were ratiometric linear Hall effect sensors available from Allegro MicroSystems, Inc., model no. A1321. FIG. 13 also provides a top view 270 of the post 204, showing the curvature of the post to accommodate the target magnet 205. The needle 254 was flexed by increasing levels away from the post 204. Sensor array readings, $S_H$, which can be converted to a location parameter by simple geometric conversion based upon the ultrasound device, are provided in the Table 1, below. Data in each row were obtained with the same fixed position of the needle.

TABLE 1

| | Level H | | | | | | | | | | | | | | | | |
|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 |
| Meter readings | 702.5 | 699 | 696 | 692 | 689 | | | | | | | | | | | | |
| $S_H$ | 611 | 608 | 605 | 602 | 599 | 596 | 594 | | | | | | | | | | |
| | 520 | 517 | 514 | 511 | 509 | 507 | 506 | 504 | 502 | 500 | 499 | 497 | 496 | | | | |
| | 460 | 458 | 455 | 453 | 451 | 449 | 447 | 446 | 444 | 443 | 442 | 441 | 440 | 439 | 437 | | |
| | 401 | 399 | 397 | 394 | 393 | 391 | 389 | 386 | 384 | 383 | 381 | 380 | 378 | 377 | 376 | 375 | 374 |

As shown, flexing the needle (the more the needle is bent the higher is level number H) reduces the sensor readings $S_H$.

Best fit of the data, with precision better than 0.3 mm for levels from 0 to 10, and better than 0.6 mm for levels 11-16) provided the following equation:

$$S_O = S_H + (a*H+c)*L_B + b*H + d$$

where
a=−0.051;
b=4.31;
c=0.0276;
d=−0.534.

Example 2

Figure 14:
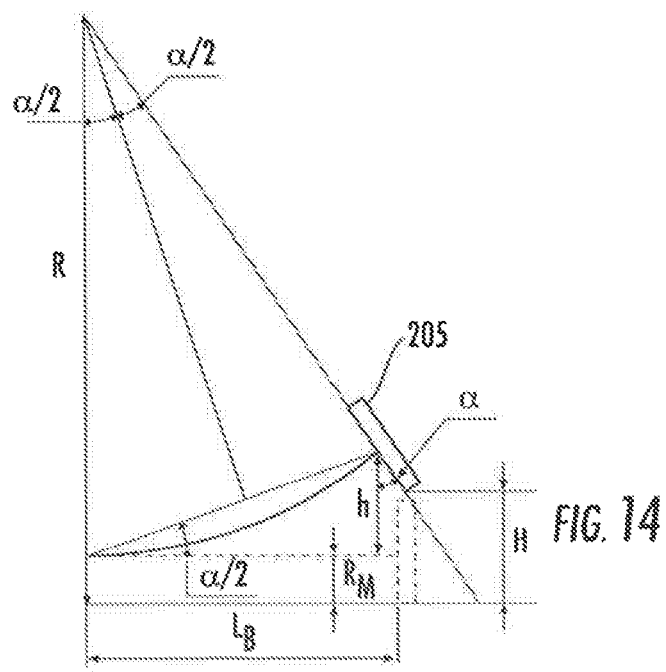
FIG. 14 illustrates a geometric description of a magnet tilt calculation model, as described herein.

FIG. 14 illustrates a geometric model utilized to describe the tilt of a target magnet with the flexing of an attached probe from alignment with a probe guide. An assumption was made that the needle was bent with a constant radius of R. (In this example, the value for the level index, H, has been converted to the distance from the sensor array to the magnet.) The following equations can be written:

$$L_B = R*\alpha$$

$$h = 2R*\sin^2(\alpha/2)$$

$$h + R_M = H + R_M*\cos(\alpha)$$

$R_M$ is the magnet radius (11 mm in this example). Thus, $$H = [L_B*\sin^2(\alpha/2)]/\alpha - R_M*\cos(\alpha)$$

This equation was solved digitally, and the results for the values of α (in radians) are shown in Table 2, below.

TABLE 2

| H (mm) | $L_B$ = 68 mm | $L_B$ = 58 mm | $L_B$ = 48 mm | $L_B$ = 38 mm | $L_B$ = 28 mm |
|---|---|---|---|---|---|
| 0 | 0 | 0 | 0 | 0 | 0 |
| 3.5 | 3.34 | 3.9 | 4.68 | 5.84 | 7.76 |
| 5.5 | 6.6 | 7.7 | 9.22 | 11.44 | 14.92 |

TABLE 2-continued

| H (mm) | $L_B$ = 68 mm | $L_B$ = 58 mm | $L_B$ = 48 mm | $L_B$ = 38 mm | $L_B$ = 28 mm |
|---|---|---|---|---|---|
| 7.5 | 9.84 | 11.44 | 13.64 | 16.78 | 21.64 |
| 9.5 | 13.04 | 15.14 | 17.96 | 21.96 | 28 |
| 11.5 | 16.2 | 18.76 | 22.2 | 27.02 | |
| 13.5 | 19.34 | 22.34 | 26.38 | | |

Figure 15:
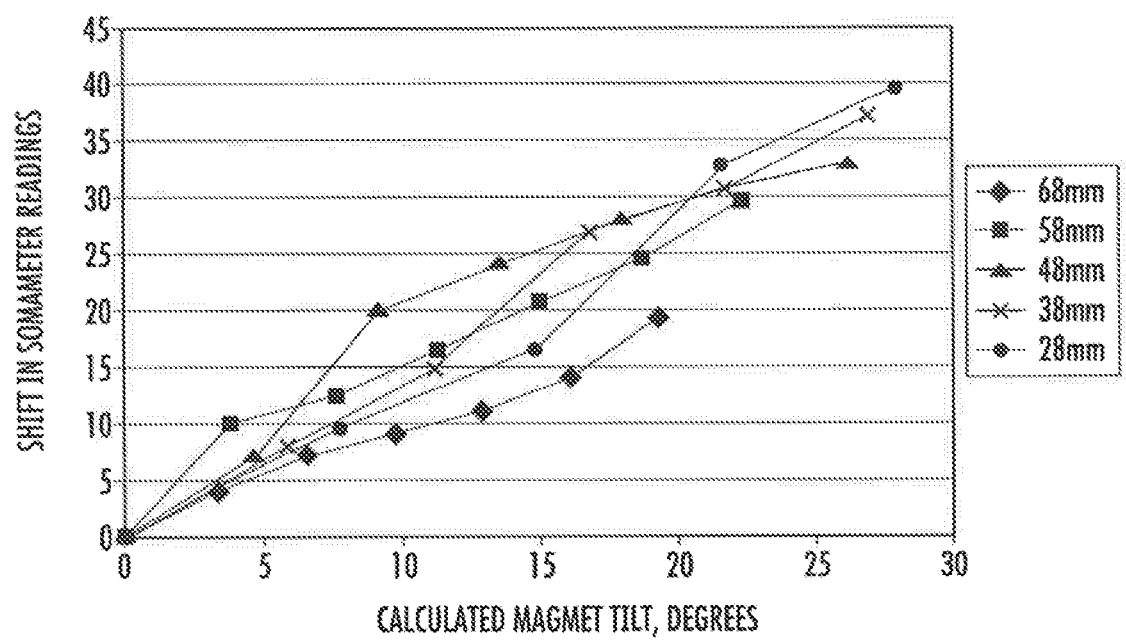
FIG. 15 graphically illustrates the shift in sensor readings upon flex in a probe as a function of the tilt of a target magnet.

The results of Examples 1 and 2 were combined to provide a graph (FIG. 15) illustrating the experimentally obtained values for the shift in the sensor reading due to the flexing of the needle ($S_O - S_H$) depend upon the angle of the flex, a. As can be seen with reference to FIG. 15, the sensor reading shift can not be explained only by the tilt of the magnet, this shift also depends upon the distance between the magnet and the sensors. Disclosed methods provide a route for accounting for this shift during the formation of a virtual image and correlating the position of a virtual image of a probe created on a monitor with the actual location of a subdermal probe.

Example 3

A second set of data for $S_H$, the output of the Hall effect sensor array, were obtained utilizing a system similar to that described above in Example 1. Raw data is provided below in Table 3. Best fit of the data provided values of the correlation factors a=−0.051 and b=4.26. Thus, the correlation equations are as follows (the values for $S_{offs}$ and $S_H$ are in units of 0.1 mm, hence the conversion factor in the equation):

$$L_B = (S_{offs} - S_H)/10 - L_C,$$

$$S_O = S_H + (4.26 - 0.051*L_B)*H,$$

TABLE 3

| H (mm) | $L_B$ = 68 mm | $L_B$ = 58 mm | $L_B$ = 48 mm | $L_B$ = 38 mm | $L_B$ = 28 mm |
|---|---|---|---|---|---|
| 0 | 203 | 306 | 404 | 501 | 597.5 |
| 3.5 | 199 | 296 | 397 | 493 | 588 |
| 5.5 | 196 | 293.5 | 384 | 486 | 581 |
| 7.5 | 194 | 289.5 | 380 | 474 | 565 |
| 9.5 | 192 | 285.5 | 376 | 470 | 558 |
| 11.5 | 189 | 281.5 | 373 | 464 | |
| 13.5 | 184 | 276.5 | 371 | | |

Utilizing these correlation factors in the processing software, a test was run. A needle of length 88.9 mm (3.5 inches) was used. A value of $S_{offs}$ was determined to be 685. A value of $L_C$ was determined to be 20.9 mm.

A device as illustrated in FIG. 13 including a detector was used. The detector provided the following readings:
$S_H = 400$

H=5

From equation 1:

$$L_B = (685-400)/10 + 21.0 = 49.5 \text{ (mm)}$$

From equation 2:

$$S_0 - S_H = (4.26 - 0.051 * 49.5) * 5 = 8.7$$

Through use of the correlation factors, the actual needle was determined to protrude from the ultrasound device by a value of $$dL_B = (S_0 - S_H)/10 = 0.87 \text{ mm}$$

more than is determined by the meter with no correlation of the reading $S_H$. This determination was confirmed by actual measurement of the protrusion. Accordingly, when forming a virtual image of the needle on an ultrasound image, the location of the virtual needle tip can be accurately located with use of the correlation factors in the processing component of the system.

Example 4

The system and correlation factors of Example 3 were utilized. Parameters measured by the detector included:
$S_H$=550
H=3

From equation 1:

$$L_B = (685-550)/10 + 21.0 = 34.5 \text{ (mm)}$$

From equation 2:

$$S_0 - S_H = (4.26 - 0.051 * 34.5) * 3 = 7.5$$

and $$dL_B = (S_0 - S_H)/10 = 0.75 \text{ mm}$$

This determined value was confirmed through actual measurement of the distance from the detector target to the tip of the needle.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. Methodology for an ultrasound system for displaying information about a probe relative to a subdermal site during a medical procedure, comprising:
   providing an ultrasound transducer configured to emit sound waves in a scanned plane into a subject;
   operating the ultrasound transducer for formation of a sonogram image of a subdermal site of the subject on a monitor based on information communicated from the ultrasound transducer;
   providing a probe assembly, comprising a subdermal probe having a subdermal probe tip at a first end thereof with at least said subdermal probe tip being adapted for movement from an exterior field into a subdermal site of the subject, and comprising an associated magnetically-based target having a magnetic field strength that is non-contact detectable by a magnetic field detector;
   providing a magnetic field detector associated with the ultrasound transducer and operated to produce data about the position of the probe assembly relative to the subdermal site of the subject on a monitor; and
   providing a processor for receiving such data from the magnetic field detector, for calculating the location of the subdermal probe tip, and for displaying in real time with the sonogram image on the monitor a virtual image showing the calculated location of the subdermal probe tip relative to the subdermal site of a subject shown on the monitor.

2. Methodology as in claim 1, wherein the magnetically-based target includes at least one magnet, and the magnetic field detector includes a plurality of sensors that are sensitive to a magnetic field generated by the at least one magnet.

3. Methodology as in claim 2, wherein the sensors comprise an array of Hall effect sensors for detecting relative to the ultrasound transducer the location of the subdermal probe tip during insertion thereof into a subject.

4. Methodology as in claim 2, further including the step of decreasing the center to center distance between adjacent sensors for increased accuracy of the magnetic field detector.

5. Methodology as in claim 2, wherein said plurality of sensors produce respective analog outputs, which are fed to an analog-to-digital converter that converts the sensor outputs into digital signals which are fed as data from the magnetic field detector to the processor.

6. Methodology as in claim 5, wherein said processor compares values of said digital signals to determine respective higher values for correspondingly determining the subdermal probe tip location.

7. Methodology as in claim 5, wherein said processor fits values of said digital signals to a nonlinear function to determine respective values for correspondingly determining the subdermal probe tip location.

8. Methodology as in claim 7, wherein said nonlinear function used with said processor comprises Gaussian distribution approximations based on data values from at least three adjacent sensors.

9. Methodology as in claim 5, wherein said processor processes values of said digital signals in conjunction with at least one offset value, for correspondingly determining the subdermal probe tip location.

10. Methodology as in claim 9, wherein said at least one offset value is used to account for ultrasound device shape and specific sensor placement resulting during manufacturing for a particular ultrasound system.

11. Methodology as in claim 9, further including:
    associating a probe guide with the ultrasound transducer, for defining a path in a known direction relative to the ultrasound transducer, for guidance of the subdermal probe by a user along such path, with the position of the probe tip tracked by the magnetic field detector; and
    wherein said at least one offset value is used to account for the distance from a surface of said probe guide to the location of the plurality of sensors.

12. Methodology as in claim 9, further including:
    a sterilizable shield having at least one skin contacting surface, with such shield containing and in contact with the ultrasound transducer; and
    wherein said at least one offset value is used to account for the distance from such surface and the plurality of sensors.

13. Methodology as in claim 1, wherein the ultrasound transducer is contained in a housing having a base with at least one skin contacting surface.

14. Methodology as in claim 13, wherein the skin contacting surface is provided at an angle in a range from about 0° to about 30° relative to the axis of the probe.

15. Methodology as in claim 14, wherein the skin contacting surface includes at least one of a flat or curved surface which has a footprint having a length extending in between about 0.5 inches and about 6 inches, and having a width at its greatest width of up to more than 2 inches.

16. Methodology as in claim 15, wherein the skin contacting surface footprint has a shape that is at least one of geometric or particularly designed to fit specific locations of a subject's anatomy.

17. Methodology as in claim 1, wherein the ultrasound transducer is at least partially enclosed in a sterilizable shield which is at least partly formed of an ultrasonic transmissive, pliant or moldable, sterilizable polymeric material.

18. Methodology as in claim 1, further including the step of selectively clamping the subdermal probe into place relative to the ultrasound transducer whenever the subdermal probe tip is situated in a desired location relative to the subdermal site of a subject, to facilitate performance of a procedure with the subdermal probe.

19. Methodology as in claim 18, further including the step of conducting a procedure with the clamped subdermal probe, including at least one of catheterization, centesis, biopsy, puncture, drain placement, injection, central vascular access, and anesthesia procedures.

20. Methodology as in claim 1, further including associating a probe guide with the ultrasound transducer, for defining a path in a known direction relative to the ultrasound transducer, for guidance of the subdermal probe by a user along such path, with the position of the probe tip tracked by the magnetic field detector.

21. Methodology as in claim 20, further including providing a housing for the ultrasound transducer, and removably attaching the probe guide to the housing.

22. Methodology as in claim 20, wherein such path is one of parallel to, coincident with, and intersecting with the scanned plane of a subject.

23. Methodology as in claim 1, further including calculating a path of the subdermal probe tip and displaying the calculated path of the subdermal probe tip relative to the subdermal site of a subject shown on the monitor.

24. Methodology as in claim 1, wherein said probe assembly has a second end thereof, and said target is associated with said second end of said probe assembly.

25. Methodology as in claim 24, wherein said target comprises one of a permanent magnet, a plurality of magnets, an array of permanent magnets, a single thin magnet, and a composition of magnetic material.

26. Methodology as in claim 25, wherein said target comprises one of at least a portion of said subdermal probe, and a device removably attachable to at least a portion of said subdermal probe.

27. Methodology as in claim 25, wherein said target comprises at least one magnet having a circular cross section, and with an axis of said circular cross section being aligned with said probe.

28. Methodology as in claim 25, wherein said target comprises at least one permanent magnet having a magnetic field strength that is electronically, non-contact detectable by said magnetic field detector up to a range up to 13.5 millimeters from said target.

29. Methodology as in claim 1, wherein said subdermal probe comprises one of a needle, tube, biopsy needle, and blade that can be guided to a subdermal location of an associated subject.

30. Methodology as in claim 1, further comprising a reservoir that is attachable to said probe.

31. Methodology as in claim 1, further comprising:
providing a housing containing said ultrasound transducer;
providing said magnetic field detector as a plurality of sensors, supported by said housing.

32. Methodology as in claim 1, wherein said step of displaying said virtual image includes accounting for a known length of said subdermal probe and for a known distance between said target and said subdermal probe tip, whenever showing the location of the subdermal probe tip relative to the subdermal site of a subject.

33. Methodology as in claim 1, further comprising:
providing a housing for containing said ultrasound transducer; and
providing a probe guide removably attachable to said ultrasound transducer housing, for defining a path in a known direction relative to said ultrasound transducer, for guidance of said subdermal probe therein;
wherein said subdermal probe comprises a needle assembly;
said target comprises at least one magnet; and
said magnetic field detector comprises a plurality of sensors, said sensors supported by said housing, and arranged for detecting the position of said target as said subdermal probe is guided in said probe guide along the path which is one of parallel to, coincident with, and intersecting with the scanned plane of a subject.

* * * * *